United States Patent [19]
Wands et al.

[11] Patent Number: 6,001,990
[45] Date of Patent: Dec. 14, 1999

[54] ANTISENSE INHIBITION OF HEPATITIS C VIRUS

[75] Inventors: Jack R. Wands, Waban; Takaja Wakita, Winchester; Darius Moradpour, Charlestown, all of Mass.

[73] Assignee: The General Hospital Corporation, Boston, Mass.

[21] Appl. No.: 08/474,700

[22] Filed: Jun. 7, 1995

Related U.S. Application Data

[63] Continuation-in-part of application No. 08/240,382, May 10, 1994, abandoned.

[51] Int. Cl.$^6$ .............................. C07H 21/04; C12N 15/00
[52] U.S. Cl. ...................... 536/24.5; 536/24.5; 435/320.1
[58] Field of Search .............................. 536/24.5; 514/44; 435/320.1, 240.1, 6, 375

[56] References Cited

U.S. PATENT DOCUMENTS

| | | | |
|---|---|---|---|
| 3,625,214 | 12/1971 | Higuchi | 128/260 |
| 4,689,320 | 8/1987 | Kaji | 514/44 |
| 4,789,734 | 12/1988 | Pierschbacher | 530/395 |
| 4,925,673 | 5/1990 | Steiner et al. | 424/455 |
| 5,399,345 | 3/1995 | Schumacher et al. | 424/85.1 |
| 5,559,028 | 9/1996 | Humphreys | 435/240.2 |

FOREIGN PATENT DOCUMENTS

| | | |
|---|---|---|
| 2104649 | 2/1994 | Canada . |
| 0 388 232 | 3/1990 | European Pat. Off. . |
| 384566 | 8/1990 | European Pat. Off. . |
| 521318 | 1/1993 | European Pat. Off. . |
| 593290 | 4/1994 | European Pat. Off. . |
| WO 92/05760 | 4/1992 | WIPO . |
| 92/09634 | 6/1992 | WIPO . |
| 92/12992 | 8/1992 | WIPO . |
| 92/19743 | 11/1992 | WIPO . |
| 92/22310 | 12/1992 | WIPO . |
| 93/10239 | 5/1993 | WIPO . |
| 93/24656 | 12/1993 | WIPO . |
| 94/05813 | 3/1994 | WIPO . |
| 94/08002 | 4/1994 | WIPO . |

OTHER PUBLICATIONS

Westermann et al., Biomed. Biochem. Acta, 48(1):85–93, 1989.
Bennet, Science, 271:434, 1996.
Weiss, Science News, 139:108–109, 1991.
Stull et al., Pharmaceutical Research, 12(4):465–483, 1995.
Wu–Pong, Pharmaceutical Technology, 18:102–114, 1994.
Gura, Science, 270;575–577, 1995.
Miller et al., Parasitology Today, 10(3):92–97, 1994.
Rojanasakul, Advanced Drug Delivery Reviews, 18:115–131, 1996.
Brown et al., Secondary Structure of the 5' Nontranslated Regions of Hepatitis C Virus and Pestivirus Genomic RNAs, Nucleic Acids Res., 20:5041–45.
Bukh et al., Sequence analysis of the 5' noncoding region of hepatitis C virus, Proc. Natl. Acad. Sci. USA 89:4942–4946, 1992.

Engelhardt et al., Ablation of E2A in recombinant adenoviruses improves transgene persistence and decreases inflammatory response in mouse liver, Proc. Natl. Acad. Sci. USA 91:6196–6200, 1994.
Ghosh et al., Oligodeoxynucleotides as antisense inhibitors of gene expression, Prog. Nuc. Acids Res., 42:79–127, 1992.
Gossen et al., Tight control of gene expression in mammalian cells by tetracycline–responsive promoters, Proc. Natl. Acad. Sci. USA 89:5547–5551, 1992.
Kern, Preclinical Evaluation of Antiviral Agents: In Vitro and Animal Model Testing, Antiviral Agents and Vital Diseases of Man, Raven Press, Ltd., NY, Ch. 3, pp. 87–95, 1990.
Matsukura et al., Phosphorothioate analogs of oligodeoxynucleotides: Inhibitors of replication and cytopathic effects of human immunodeficiency virus, Proc. Natl. Acad. Sci. USA 84:7706–7710, 1987.
Milligan et al., Current concepts in antisense drug design, J. Med. Chem. 36(14):1923–1937, 1993.
Uhlmann et al., Antisense Oligonucleotides: A new therapeutic principle, Chemical Reviews 90(4):543–584, 1990.
Von Ruden et al., Inhibition of Human T–Cell Leukemia Virus Type I Replication in Primary Human T Cells that Express Antisense RNA, J. Virology, 63:677–82, 1989.
Wagner, Richard W., Gene inhibition using antisense of oligodeoxynucleotides, Nature 372:333–335, 1994.
Wakita et al., Specific inhibition of hepatitis C virus expression by antisense oligodeoxynucleotides, J. Biol. Chem. 269(19):14205–14210, 1994.
Wolff et al., Direct gene transfer into mouse muscle in vivo, Science 247:1465–1468, 1990.
Benoist et al., In Vivo Sequence Requirements of the SV40 Early Promoter Region, Nature 290:304–10, 1981.
Blum et al., Inhibition of Hepatitis B Virus by Antisense Oligodeoxynucleotides, Lancet 337:1230, 1991.
Brown et al., Secondary Structure of the 5'Nontranslated Regions of Hepatitis C Virus and Pestivirus Genomic RNAs, Nucleic Acids Research 20:5041–5045, 1992.
Choo et al., Genetic Organization and Diversity of the Hepatitis C Virus, Proc. Natl. Acad. Sci. USA 88:2451–2455, 1991.
Crooke, Therapeutic Applications of Oligonucleotides, Annu. Rev. Pharmacol. Toxicol. 32:329–76, 1992.
DeBernardi et al., Inhibition of cAMP Accumulation by Intracellular Calcium Mobilization in C6–2B Cells Stably Transfected with Substance K Receptor cDNA, Proc. Natl. Acad. Sci. USA 88:9257–9261, 1991.
Dolnick, Commentary: Antisense Agents in Pharmacology, Biochemical Pharmacology 40:671–675, 1990.

(List continued on next page.)

*Primary Examiner*—Brian R. Stanton
*Assistant Examiner*—Deborah J. R. Clark
*Attorney, Agent, or Firm*—Fish & Richardson P.C.

[57] ABSTRACT

The invention features antisense oligonucleotides and methods of using these antisense oligonucleotides for inhibiting HCV RNA translation.

31 Claims, 11 Drawing Sheets

OTHER PUBLICATIONS

Goodarzi et al., Antisense Oligodeoxyribonucleotides Inhibit the Expression of the Gene for Hepatitis B Virus Surface Antigen, J. General Virology 71:3021–3025, 1990.

Graham et al., Characteristics of a Human Cell Line Transformed by DNA from Human Adenovirus Type 5, J. Gen. Virology 36:59–72, 1977.

Hamer and Walling, Regulation In Vivo of a Cloned Mammalian Gene: Cadmium Induces the Transcription of a Mouse Metallothionein Gene in SV40 Vectors, J. Molecular and Applied Genetics 1:273–288, 1982.

Han et al., Characterization of the Terminal Regions of Hepatitis C Viral RNA: Identification of Conserved Sequences . . . Region and poly(A) Tails at the 3' End, Proc. Natl. Acad. Sci. USA 88:1711–1715, 1991.

Hijikata et al., Gene Mapping of the Putative Structural Region of the Hepatitis C Virus Genome by in Vitro Processing Analysis, Proc. Natl. Acad. Sci. USA 88:5547–5551, 1991.

Hoofnagle et al., Treatment of Chronic Non–A, Non–B Hepatitis with Recombinant Human Alpha Interferon, N. Eng. J. Med. 315:1575–1578, 1986.

Inchauspe et al., Genomic Structure of the Human Prototype Strain H of Hepatitis C Virus: Comparison with American and Japanese Isolates, Proc. Natl. Acad. Sci. USA 88:10292–10296, 1991.

Kabanov et al., A New Class of Antivirals: Antisense Oligonucleotides Combined with a Hydrophobic . . . Reproduction and Synthesis of Virus–Specific Proteins in MDCK Cells, Febs Letters, 259:327–330, 1990.

Kiyosawa et al., Interrelationship of Blood Transfusion, Non–A, Non–B Hepatitis and Hepatocellular Carcinoma: Analysis by Detection of Antibody to Hepatitis C Virus, Hepatology 12:671–675, 1990.

Kotin et al., Site–specific Integration by Adeno–associated Virus, Proc. Natl. Acad. Sci. USA 87:2211–2215, 1990.

Kuo et al., An Assay for Circulating Antibodies to a Major Etiologic Virus of Human Non–A, Non–B Hepatitis, Science 244:362–364, 1989.

Le Doan et al., Antisense Oligonucleotides as Potential Antiviral and Anticancer Agents, Bull. Cancer 76:849–852, 1989.

Lemaitre et al., Specific Antiviral Activity of a Poly(L–lysine)–conjugated Oligodeoxyribonucleotide . . . Vesicular Stomatitis Virus N Protein mRNA Initiation Site, Proc. Natl. Acad. Sci. USA 84:648–652, 1987.

Lisziewicz et al., Specific Inhibition of Human Immunodeficiency Virus Type 1 Replication by Antisense Oligonucleotides: An In Vitro Model for Treatment, Proc. Natl. Acad. Sci. USA 89:11209–11213, 1992.

McKnight, Functional Relationships Between Transcriptional Control Signals of the Thymidine Kinase Gene of Herpes Simplex Virus, Cell 31:355–365, 1982.

Morsy et al., Efficient Adenoviral Gene Transduction in Human and Mouse Hepatocytes In Vitro and in Mouse Liver In Vivo, J. Cell. Biochem., Suppl. 17E:SZ109, 1993.

Offensperger et al., In Vivo Inhibition of Duck Hepatitis B Virus Replication and Gene Expression by Phosphorothioate Modified Antisense Oligodeoxynucleotides, Embo J. 12:1257–1262, 1993.

Okamoto et al., Nucleotide Sequence of the Genomic RNA of Hepatitis C Virus Isolated from a Human Carrier: Comparison with Reported Isolates for Conserved and Divergent Regions, J. Gen. Virol. 72:2697–2704, 1991.

Okamoto et al., Full–Length Sequence of a Hepatitis C Virus Genome Having Poor Homology to Reported Isolates: Comparative Study of Four Distinct Genotypes, Virology 188:331–341, 1992.

Rosenberg et al., Gene Transfer into Humans—Immunmotherapy of Patients with Advanced Melanoma, using Lung Tumor–Infiltrating Lymphocytes Modified by Retroviral Gene Transduction, N. Eng. J. Med. 323:570–578, 1990.

Smith et al., Antiviral Effect of an Oligo(nucleoside methylphosphonate) Complementary to the Splice . . . Simplex Virus Type 1 Immediate Early pre–mRNAs 4 and 5, Proc. Natl. Acad. Sci. USA 83:2787–2791, 1986.

Spiess, The Asialoglycoprotein Receptor: A Model for Endocytic Transport Receptors, Biochemistry 29:10009–10018, 1990.

Stein and Cheng, Antisense Oligonucleotides as Therapeutic Agents—Is the Bullet Really Magical, Science 261:1004–1012, 1993.

Tsukiyama–Kohara et al., Internal Ribosome Entry Site within Hepatitis C Virus RNA, J. Virology 66:1476–1483, 1992.

Wang et al., Translation of Human Hepatitis C Virus RNA in Cultured Cells is Mediated by an Internal Ribosome–Binding Mechanism, J. Virology 67:3338–3344, 1993.

Wu and Wu, Specific Inhibition of Hepatitis B Viral Gene Expression In Vitro by Targeted Antisense Oligonucleotides, J. Biol. Chem. 267:12436–12439, 1992.

Yoshioka et al., Detection of Hepatitis C Virus by Polymerase Chain Reaction and Response to Interferon–α Therapy: Relationship to Genotypes of Hepatitis C Virus, Hepatology 16:293–299, 1992.

Zamecnik et al., Inhibition of Replication and Expression of Human T–cell Lymphotropic Virus Type III in . . . Synthetic Oligonucleotides Complementary to Viral RNA, Proc. Natl. Acad. Sci. USA 83:4143–4146, 1986.

FIG. 13A  FIG. 13B
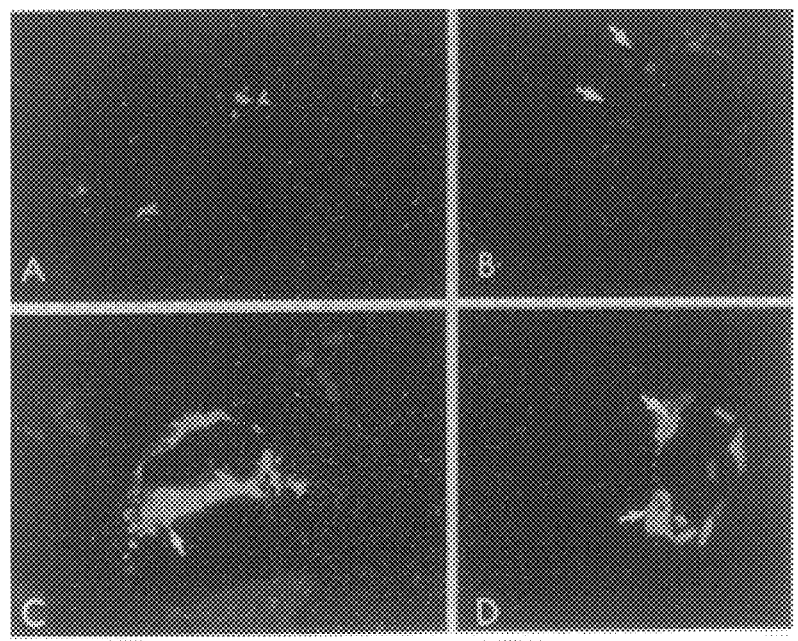
FIG. 13C  FIG. 13D
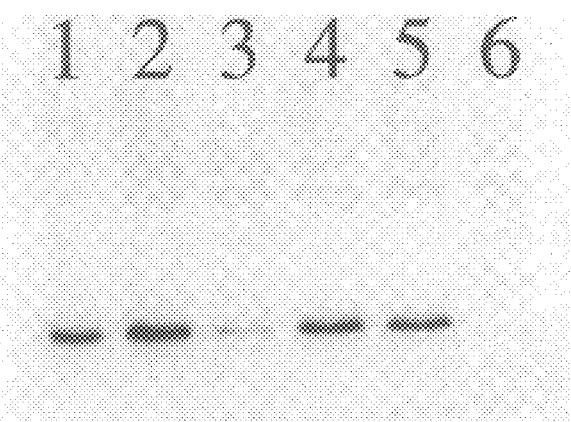
FIG. 14

| | | | | | |
|---|---|---|---|---|---|
| GCCAGCCCCC | GATTGGGGGC | GACACTCCAC | CATAGATCAC | TCCCCTGTGA | GGAACTACTG | 60 |
| TCTTCACGCA | GAAAGCGTCT | AGCCATGGCG | TTAGTATGAG | TGTCGTGCAG | CCTCCAGGAC | 120 |
| CCCCCTCCC | GGGAGAGCCA | TAGTGGTCTG | CGAACCGGT | GAGTACACCG | GAATTGCCAG | 180 |
| GACGACCGGG | TCCTTTCTTG | GATCAACCCG | CTCAATGCCT | GGAGATTTGG | GCGTGCCCCC | 240 |
| GCGAGACTGC | TAGCCGAGTA | GTGTTGGGTC | GCGAAAGGCC | TTGTGGTACT | GCCTGATAGG | 300 |
| GTGCTTGCGA | GTGCCCCGGG | AGGTCTCGTA | GACCGTGCAC | CATGAGCACG | AATCCTAAAC | 360 |
| CTCAAAGAAA | AACCAAACGT | AACACCAACC | GCCGCCCACA | GGACGTCAAG | TTCCCGGGCG | 420 |
| GTGGTCAGAT | CGTTGGTGGA | GTTTACCTGT | TGCCGCGCAG | GGGCCCCAGG | TTGGGTGTGC | 480 |
| GCGCGACTAG | GAAGACTTCC | GAGCGGTCGC | AACCTCGTGG | AAGGCGACAA | CCTATCCCCA | 540 |
| AGGATCGCCG | GCCCGAGGGC | AGGGCCTGGG | CTCAGCCTTG | GTACCCTTGG | CCCCTCTATG | 600 |
| GCAACGAGGG | CATGGGGTGG | GCAGGATGGC | TCCTGTCACC | CCGTGGCTCC | CGGCCTAGTT | 660 |
| GGGCCCCAA | TGACCCCCGG | CGTAGGTCGC | GTAATTTGGG | TAAAGTCATC | GATACCCTTA | 720 |
| CATGCGGCTT | CGCCGACCTC | ATGGGGTAGA | TTCCGCTCGT | CGGCGCTCCC | TTGGGGGCG | 780 |

FIG. 15 (SEQ ID NO:45)

SEQUENCE LISTING (1) GENERAL INFORMATION:

(iii) NUMBER OF SEQUENCES: 45

(2) INFORMATION FOR SEQ ID NO: 1:

(i) SEQUENCE CHARACTERISTICS:
       (A) LENGTH: 28
       (B) TYPE: nucleic acid
       (C) STRANDEDNESS: single
       (D) TOPOLOGY: linear (xi) SEQUENCE DESCRIPTION: SEQ ID NO: 1:

ATCTATGGTG GAGTGTCGCC CCCAATCG                                    28

(2) INFORMATION FOR SEQ ID NO: 2:

(i) SEQUENCE CHARACTERISTICS:
       (A) LENGTH: 28
       (B) TYPE: nucleic acid
       (C) STRANDEDNESS: single
       (D) TOPOLOGY: linear (xi) SEQUENCE DESCRIPTION: SEQ ID NO: 2:

GAAGACAGTA GTTCCTCACA GGGGAGTG                                    28

(2) INFORMATION FOR SEQ ID NO: 3:

(i) SEQUENCE CHARACTERISTICS:
       (A) LENGTH: 28
       (B) TYPE: nucleic acid
       (C) STRANDEDNESS: single
       (D) TOPOLOGY: linear (xi) SEQUENCE DESCRIPTION: SEQ ID NO: 3:

TAGACGCTTT CTGCGTGAAG ACAGTAGT                                    28

(2) INFORMATION FOR SEQ ID NO: 4:

(i) SEQUENCE CHARACTERISTICS:
       (A) LENGTH: 28
       (B) TYPE: nucleic acid
       (C) STRANDEDNESS: single
       (D) TOPOLOGY: linear (xi) SEQUENCE DESCRIPTION: SEQ ID NO: 4:

ACACTCATAC TAACGCCATG GCTAGACG                                    28

(2) INFORMATION FOR SEQ ID NO: 5:

(i) SEQUENCE CHARACTERISTICS:
       (A) LENGTH: 28
       (B) TYPE: nucleic acid
       (C) STRANDEDNESS: single
       (D) TOPOLOGY: linear (xi) SEQUENCE DESCRIPTION: SEQ ID NO: 5:

ACCACTATGG CTCTCCCGGG AGGGGGGG                                    28

(2) INFORMATION FOR SEQ ID NO: 6:

(i) SEQUENCE CHARACTERISTICS:
       (A) LENGTH: 28
       (B) TYPE: nucleic acid
       (C) STRANDEDNESS: single
       (D) TOPOLOGY: linear (xi) SEQUENCE DESCRIPTION: SEQ ID NO: 6:

CACCGGTTCC GCAGACCACT ATGGCTCT                                              28

(2) INFORMATION FOR SEQ ID NO:    7:

(i) SEQUENCE CHARACTERISTICS:
        (A) LENGTH:    28
        (B) TYPE: nucleic acid
        (C) STRANDEDNESS:    single
        (D) TOPOLOGY:   linear (xi) SEQUENCE DESCRIPTION: SEQ ID NO: 7:

AATTCCGGTG TACTCACCGG TTCCGCAG                                              28

(2) INFORMATION FOR SEQ ID NO:    8:

(i) SEQUENCE CHARACTERISTICS:
        (A) LENGTH:    28
        (B) TYPE: nucleic acid
        (C) STRANDEDNESS:    single
        (D) TOPOLOGY:   linear (xi) SEQUENCE DESCRIPTION: SEQ ID NO: 8:

GCGGGTTGAT CCAAGAAAGG ACCCGGTC                                              28

(2) INFORMATION FOR SEQ ID NO:    9:

(i) SEQUENCE CHARACTERISTICS:
        (A) LENGTH:    28
        (B) TYPE: nucleic acid
        (C) STRANDEDNESS:    single
        (D) TOPOLOGY:   linear (xi) SEQUENCE DESCRIPTION: SEQ ID NO: 9:

GCGGGGGCAC GCCCAAATCT CCAGGCAT                                              28

(2) INFORMATION FOR SEQ ID NO:   10:

(i) SEQUENCE CHARACTERISTICS:
        (A) LENGTH:    28
        (B) TYPE: nucleic acid
        (C) STRANDEDNESS:    single
        (D) TOPOLOGY:   linear (xi) SEQUENCE DESCRIPTION: SEQ ID NO: 10:

GACCCAACAC TACTCGGCTA GCAGTCTC                                              28

(2) INFORMATION FOR SEQ ID NO:   11:

(i) SEQUENCE CHARACTERISTICS:
        (A) LENGTH:    28
        (B) TYPE: nucleic acid
        (C) STRANDEDNESS:    single
        (D) TOPOLOGY:   linear (xi) SEQUENCE DESCRIPTION: SEQ ID NO: 11:

TATCAGGCAG TACCACAAGG CCTTTCGC                                              28

(2) INFORMATION FOR SEQ ID NO:   12:

(i) SEQUENCE CHARACTERISTICS:
        (A) LENGTH:    28
        (B) TYPE: nucleic acid
        (C) STRANDEDNESS:    single
        (D) TOPOLOGY:   linear (xi) SEQUENCE DESCRIPTION: SEQ ID NO: 12:

```
ACTCGCAAGC ACCCTATCAG GCAGTACC                                              28

(2) INFORMATION FOR SEQ ID NO:    13:

(i) SEQUENCE CHARACTERISTICS:
        (A) LENGTH:    28
        (B) TYPE: nucleic acid
        (C) STRANDEDNESS:   single
        (D) TOPOLOGY:  linear (xi) SEQUENCE DESCRIPTION: SEQ ID NO: 13:

AGACCTCCCG GGGCACTCGC AAGCACCC                                              28

(2) INFORMATION FOR SEQ ID NO:    14:

(i) SEQUENCE CHARACTERISTICS:
        (A) LENGTH:    28
        (B) TYPE: nucleic acid
        (C) STRANDEDNESS:   single
        (D) TOPOLOGY:  linear (xi) SEQUENCE DESCRIPTION: SEQ ID NO: 14:

TGCACGGTCT ACGAGACCTC CCGGGGCA                                              28

(2) INFORMATION FOR SEQ ID NO:    15:

(i) SEQUENCE CHARACTERISTICS:
        (A) LENGTH:    28
        (B) TYPE: nucleic acid
        (C) STRANDEDNESS:   single
        (D) TOPOLOGY:  linear (xi) SEQUENCE DESCRIPTION: SEQ ID NO: 15:

GTGCTCATGG TGCACGGTCT ACGAGACC                                              28

(2) INFORMATION FOR SEQ ID NO:    16:

(i) SEQUENCE CHARACTERISTICS:
        (A) LENGTH:    27
        (B) TYPE: nucleic acid
        (C) STRANDEDNESS:   single
        (D) TOPOLOGY:  linear (xi) SEQUENCE DESCRIPTION: SEQ ID NO: 16:

CTTTGAGGTT TAGGATTCGT GCTCATG                                               27

(2) INFORMATION FOR SEQ ID NO:    17:

(i) SEQUENCE CHARACTERISTICS:
        (A) LENGTH:    27
        (B) TYPE: nucleic acid
        (C) STRANDEDNESS:   single
        (D) TOPOLOGY:  linear (xi) SEQUENCE DESCRIPTION: SEQ ID NO: 17:

TTTGGTTTTT CTTTGAGGTT TAGGATT                                               27

(2) INFORMATION FOR SEQ ID NO:    18:

(i) SEQUENCE CHARACTERISTICS:
        (A) LENGTH:    27
        (B) TYPE: nucleic acid
        (C) STRANDEDNESS:   single
        (D) TOPOLOGY:  linear (xi) SEQUENCE DESCRIPTION: SEQ ID NO: 18:

TGGTGTTACG TTTGGTTTTT CTTTGAG                                               27
```

```
(2) INFORMATION FOR SEQ ID NO:    19:

(i) SEQUENCE CHARACTERISTICS:
        (A) LENGTH:    27
        (B) TYPE: nucleic acid
        (C) STRANDEDNESS:    single
        (D) TOPOLOGY:  linear (xi) SEQUENCE DESCRIPTION: SEQ ID NO: 19:

GTAAACTCCA CCAACGATCT GACCACC                                           27

(2) INFORMATION FOR SEQ ID NO:    20:

(i) SEQUENCE CHARACTERISTICS:
        (A) LENGTH:    22
        (B) TYPE: nucleic acid
        (C) STRANDEDNESS:    single
        (D) TOPOLOGY:  linear (xi) SEQUENCE DESCRIPTION: SEQ ID NO: 20:

TTTGGTTTTT CTTTGAGGTT TA                                                22

(2) INFORMATION FOR SEQ ID NO:    21:

(i) SEQUENCE CHARACTERISTICS:
        (A) LENGTH:    17
        (B) TYPE: nucleic acid
        (C) STRANDEDNESS:    single
        (D) TOPOLOGY:  linear (xi) SEQUENCE DESCRIPTION: SEQ ID NO: 21:

TTTGGTTTTT CTTTGAG                                                      17

(2) INFORMATION FOR SEQ ID NO:    22:

(i) SEQUENCE CHARACTERISTICS:
        (A) LENGTH:    12
        (B) TYPE: nucleic acid
        (C) STRANDEDNESS:    single
        (D) TOPOLOGY:  linear (xi) SEQUENCE DESCRIPTION: SEQ ID NO: 22:

TTTGGTTTTT CT                                                           12

(2) INFORMATION FOR SEQ ID NO:    23:

(i) SEQUENCE CHARACTERISTICS:
        (A) LENGTH:    22
        (B) TYPE: nucleic acid
        (C) STRANDEDNESS:    single
        (D) TOPOLOGY:  linear (xi) SEQUENCE DESCRIPTION: SEQ ID NO: 23:

TTTTTCTTTG AGGTTTAGGA TT                                                22

(2) INFORMATION FOR SEQ ID NO:    24:

(i) SEQUENCE CHARACTERISTICS:
        (A) LENGTH:    17
        (B) TYPE: nucleic acid
        (C) STRANDEDNESS:    single
        (D) TOPOLOGY:  linear (xi) SEQUENCE DESCRIPTION: SEQ ID NO: 24:

CTTTGAGGTT TAGGATT                                                      17
```

```
(2) INFORMATION FOR SEQ ID NO:    25:

(i) SEQUENCE CHARACTERISTICS:
        (A) LENGTH:    12
        (B) TYPE: nucleic acid
        (C) STRANDEDNESS:    single
        (D) TOPOLOGY:   linear (xi) SEQUENCE DESCRIPTION: SEQ ID NO: 25:

AGGTTTAGGA TT                                                             12

(2) INFORMATION FOR SEQ ID NO:    26:

(i) SEQUENCE CHARACTERISTICS:
        (A) LENGTH:    12
        (B) TYPE: nucleic acid
        (C) STRANDEDNESS:    single
        (D) TOPOLOGY:   linear (xi) SEQUENCE DESCRIPTION: SEQ ID NO: 26:

CTTTGAGGTT TA                                                             12

(2) INFORMATION FOR SEQ ID NO:    27:

(i) SEQUENCE CHARACTERISTICS:
        (A) LENGTH:    10
        (B) TYPE: nucleic acid
        (C) STRANDEDNESS:    single
        (D) TOPOLOGY:   linear (xi) SEQUENCE DESCRIPTION: SEQ ID NO: 27:

AGGTTTAGGA                                                                10

(2) INFORMATION FOR SEQ ID NO:    28:

(i) SEQUENCE CHARACTERISTICS:
        (A) LENGTH:    10
        (B) TYPE: nucleic acid
        (C) STRANDEDNESS:    single
        (D) TOPOLOGY:   linear (xi) SEQUENCE DESCRIPTION: SEQ ID NO: 28:

GTTTAGGATT                                                                10

(2) INFORMATION FOR SEQ ID NO:    29:

(i) SEQUENCE CHARACTERISTICS:
        (A) LENGTH:    28
        (B) TYPE: nucleic acid
        (C) STRANDEDNESS:    single
        (D) TOPOLOGY:   linear (xi) SEQUENCE DESCRIPTION: SEQ ID NO: 29:

CACTCCCCTG TGAGGAACTA CTGTCTTC                                            28

(2) INFORMATION FOR SEQ ID NO:    30:

(i) SEQUENCE CHARACTERISTICS:
        (A) LENGTH:    28
        (B) TYPE: nucleic acid
        (C) STRANDEDNESS:    single
        (D) TOPOLOGY:   linear (xi) SEQUENCE DESCRIPTION: SEQ ID NO: 30:

ACTACTGTCT TCACGCAGAA AGCGTCTA                                            28

(2) INFORMATION FOR SEQ ID NO:    31:
```

(i) SEQUENCE CHARACTERISTICS:
    (A) LENGTH:   28
    (B) TYPE: nucleic acid
    (C) STRANDEDNESS:   single
    (D) TOPOLOGY: linear (xi) SEQUENCE DESCRIPTION: SEQ ID NO: 31:

CGTCTAGCCA TGGCGTTAGT ATGAGTGT                                              28

(2) INFORMATION FOR SEQ ID NO:   32:

(i) SEQUENCE CHARACTERISTICS:
        (A) LENGTH:   28
        (B) TYPE: nucleic acid
        (C) STRANDEDNESS:   single
        (D) TOPOLOGY: linear (xi) SEQUENCE DESCRIPTION: SEQ ID NO: 32:

CCCCCCCTCC CGGGAGAGCC ATAGTGGT                                              28

(2) INFORMATION FOR SEQ ID NO:   33:

(i) SEQUENCE CHARACTERISTICS:
        (A) LENGTH:   28
        (B) TYPE: nucleic acid
        (C) STRANDEDNESS:   single
        (D) TOPOLOGY: linear (xi) SEQUENCE DESCRIPTION: SEQ ID NO: 33:

CTGCGGAACC GGTGAGTACA CCGGAATT                                              28

(2) INFORMATION FOR SEQ ID NO:   34:

(i) SEQUENCE CHARACTERISTICS:
        (A) LENGTH:   28
        (B) TYPE: nucleic acid
        (C) STRANDEDNESS:   single
        (D) TOPOLOGY: linear (xi) SEQUENCE DESCRIPTION: SEQ ID NO: 34:

GCGAAAGGCC TTGTGGTACT GCCTGATA                                              28

(2) INFORMATION FOR SEQ ID NO:   35:

(i) SEQUENCE CHARACTERISTICS:
        (A) LENGTH:   28
        (B) TYPE: nucleic acid
        (C) STRANDEDNESS:   single
        (D) TOPOLOGY: linear (xi) SEQUENCE DESCRIPTION: SEQ ID NO: 35:

GCCTGATAGG GTGCTTGCGA GTGCCCCG                                              28

(2) INFORMATION FOR SEQ ID NO:   36:

(i) SEQUENCE CHARACTERISTICS:
        (A) LENGTH:   28
        (B) TYPE: nucleic acid
        (C) STRANDEDNESS:   single
        (D) TOPOLOGY: linear (xi) SEQUENCE DESCRIPTION: SEQ ID NO: 36:

TGCCCCGGGA GGTCTCGTAG ACCGTGCA                                              28

(2) INFORMATION FOR SEQ ID NO:   37:

(i) SEQUENCE CHARACTERISTICS:
        (A) LENGTH:   29

(B) TYPE: nucleic acid
            (C) STRANDEDNESS: single
            (D) TOPOLOGY: linear (xi) SEQUENCE DESCRIPTION: SEQ ID NO: 37:

CGAAUCCUAA ACCUCAAAGA AAAACCAAA                                           29

(2) INFORMATION FOR SEQ ID NO:    38:

(i) SEQUENCE CHARACTERISTICS:
            (A) LENGTH:    29
            (B) TYPE: nucleic acid
            (C) STRANDEDNESS: single
            (D) TOPOLOGY: linear (xi) SEQUENCE DESCRIPTION: SEQ ID NO: 38:

CAAAUCCUAA ACCUCAAAGA AAAACCAAA                                           29

(2) INFORMATION FOR SEQ ID NO:    39:

(i) SEQUENCE CHARACTERISTICS:
            (A) LENGTH: 342 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:39:

TGGTGCACGG TCTACGAGAC CTCCCGGGGC ACTCGCAAGC ACCCTATCAG GCAGTACCAC          60

AAGGCCTTTC GCGACCCAAC ACTACTCGGC TAGCAGTCTC GCGGGGGCAC GCCCAAATCT         120

CCAGGCATTG AGCGGGTTGA TCCAAGAAAG GACCCGGTCG TCCTGGCAAT TCCGGTGTAC         180

TCACCGGTTC GCAGACCAC TATGGCTCTC CCGGGAGGGG GGGTCCTGGA GGCTGCACGA          240

CACTCATACT AACGCCATGG CTAGACGCTT TCTGCGTGAA GACAGTAGTT CCTCACAGGG         300

GAGTGATCTA TGGTGGAGTG TCGCCCCCAA TCGGGGGCTG GC                           342

(2) INFORMATION FOR SEQ ID NO:40:

(i) SEQUENCE CHARACTERISTICS:
            (A) LENGTH: 260 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:40:

TACTCGGCTA GCAGTCTCGC GGGGGCACGC CCAAATCTCC AGGCATTGAG CGGGTTGATC          60

CAAGAAAGGA CCCGGTCGTC CTGGCAATTC CGGTGTACTC ACCGGTTCCG CAGACCACTA        120

TGGCTCTCCC GGGAGGGGGG GTCCTGGAGG CTGCACGACA CTCATACTAA CGCCATGGCT        180

AGACGCTTTC TGCGTGAAGA CAGTAGTTCC TCACAGGGGA GTGATCTATG GTGGAGTGTC        240

GCCCCCAATC GGGGGCTGGC                                                   260

(2) INFORMATION FOR SEQ ID NO:41:

(i) SEQUENCE CHARACTERISTICS:
            (A) LENGTH: 155 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:41:

TTCCGCAGAC CACTATGGCT CTCCCGGGAG GGGGGGTCCT GGAGGCTGCA CGACACTCAT    60

ACTAACGCCA TGGCTAGACG CTTTCTGCGT GAAGACAGTA GTTCCTCACA GGGGAGTGAT    120

CTATGGTGGA GTGTCGCCCC CAATCGGGGG CTGGC    155

(2) INFORMATION FOR SEQ ID NO:42:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

GTGAAGACAG TAGTTCCTCA CAGGGGAGTG ATCTATGGTG GAGTGTCGCC CCCAATCGGG    60

GGCTGGC    67

(2) INFORMATION FOR SEQ ID NO:43:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

GGGCTGGC    8

(2) INFORMATION FOR SEQ ID NO:44:

(i) SEQUENCE CHARACTERISTICS:
        (A) LENGTH: 82 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:44:

Met Ser Thr Asn Pro Lys Pro Gln Arg Lys Thr His Arg Asn Thr Asn
1               5                   10                  15

Arg Arg Pro Pro Asp Val Lys Phe Pro Gly Gly Gly Gln Ile Val Gly
            20                  25                  30

Gly Val Tyr Leu Met Pro Arg Arg Gly Pro Lys Leu Gly Val Arg Ala
        35                  40                  45

Pro Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro (2) INFORMATION FOR SEQ ID NO:45:

(i) SEQUENCE CHARACTERISTICS:
        (A) LENGTH: 780 base pairs
        (B) TYPE: nucleic acid
        (C) STRANDEDNESS: single
        (D) TOPOLOGY: linear (xi) SEQUENCE DESCRIPTION: SEQ ID NO:45:

```
GCCAGCCCCC GATTGGGGGC GACACTCCAC CATAGATCAC TCCCCTGTGA GGAACTACTG        60

TCTTCACGCA GAAAGCGTCT AGCCATGGCG TTAGTATGAG TGTCGTGCAG CCTCCAGGAC       120

CCCCCCTCCC GGGAGAGCCA TAGTGGTCTG CGGAACCGGT GAGTACACCG GAATTGCCAG       180

GACGACCGGG TCCTTTCTTG GATCAACCCG CTCAATGCCT GGAGATTTGG GCGTGCCCCC       240

GCGAGACTGC TAGCCGAGTA GTGTTGGGTC GCGAAAGGCC TTGTGGTACT GCCTGATAGG       300

GTGCTTGCGA GTGCCCCGGG AGGTCTCGTA GACCGTGCAC CATGAGCACG AATCCTAAAC       360

CTCAAAGAAA AACCAAACGT AACACCAACC GCCGCCCACA GGACGTCAAG TTCCCGGGCG       420

GTGGTCAGAT CGTTGGTGGA GTTTACCTGT TGCCGCGCAG GGGCCCCAGG TTGGGTGTGC       480

GCGCGACTAG GAAGACTTCC GAGCGGTCGC AACCTCGTGG AAGGCGACAA CCTATCCCCA       540

AGGATCGCCG GCCCGAGGGC AGGGCCTGGG CTCAGCCTGG GTACCCTTGG CCCCTCTATG       600

GCAACGAGGG CATGGGGTGG GCAGGATGGC TCCTGTCACC CCGTGGCTCC CGGCCTAGTT       660

GGGGCCCCAA TGACCCCCGG CGTAGGTCGC GTAATTTGGG TAAAGTCATC GATACCCTTA       720

CATGCGGCTT CGCCGACCTC ATGGGGTAGA TTCCGCTCGT CGGCGCTCCC TTGGGGGCG        780
```

ANTISENSE INHIBITION OF HEPATITIS C VIRUS

The application is a continuation-in-part of application Ser. No. 08/240,382, filed May 10, 1994 now abandoned.

This invention was supported in part by the U.S. Government under grant numbers CA-35711 and AA-08169 awarded by the National Institute of Health. The Government has certain rights in the invention.

BACKGROUND OF THE INVENTION

This invention relates to antisense inhibition of translation of Hepatitis C Virus RNA.

Antisense oligonucleotides (oligos) are useful tools for studying cellular and viral gene function (Uhlmann et al., Chem. Rev. 90(4):543–584, 1990; Stein et al., Science 261:1004–1012, 1993). In addition, antisense oligonucleotides are considered to be ideal agents for inhibiting viral replication, as they can be specifically targeted to viral RNA sequences, and therefore are not likely to affect host-specific gene expression. Antisense oligonucleotides have been used in cell culture systems to inhibit the replication of a number of viruses, including HIV (Zamecnik et al., Proc. Natl. Acad. Sci. USA 83:4143–4146, 1986; Matsukura et al., Proc. Natl. Acad. Sci. USA 84:7706–7710, 1987; Lisziewicz et al., Proc. Natl. Acad. Sci. USA 89:11209–11213, 1992), influenza (Kabanov et al., FEBS Lett. 259:327–330, 1990), herpes simplex (Smith et al., Proc. Natl. Acad. Sci. USA 83:2787–2791, 1986), vesicular stomatitis (Lemaitre et al., Proc. Natl. Acad. Sci. USA 84:648–652, 1987), and hepatitis B viruses (Goodarzi et al., J. Gen. Virol. 71:3021–3025, 1990; Blum et al., Lancet 337:1230, 1991; Wu et al., J. Biol. Chem. 267(18):12436–12439, 1992; Offensperger et al., EMBO J. 12:1257–1262, 1993). The inhibitory effects of antisense oligonucleotides on viral activity is highly specific. For example, Lisziewicz et al. found that two overlapping 28 nucleotide antisense oligonucleotides inhibited HIV replication, but with a 20-fold difference in efficiency (Lisziewicz et al., Proc. Natl. Acad. Sci. USA 89:11209–11213, 1992).

Hepatitis C virus (HCV) is a positive strand RNA virus with a linear genome of about 9,500 bases. Different isolates show considerable nucleotide (nt) sequence diversity, leading to the subdivision of HCV genomes into at least eight genotypes (Simmonds et al., *J Gen Virol*, 74:2391–2399, 1993). In all genotypes the viral RNA contains a large open reading frame that encodes a polyprotein precursor of 3010–3033 amino acids (Choo et al., *Proc Natl Acad Sci USA*, 88:2451–2455, 1991). This precursor is cleaved by cellular and viral proteinases to give rise to the core (C), envelope (E1, E2) and non-structural proteins, e.g., NS2-NS5 (Selby et al., *J Gen Virol*, 74:1103–1113, 1993). The coding sequence of the RNA genome is preceded by a 5' non-coding region (NCR) of 324–341 nucleotides (Han et al., *Proc Natl Acad Sci USA*, 88:1711–1715, 1991; Bukh et al., *Proc Natl Acad Sci USA*, 89:4942–4946, 1992) which is highly conserved among all strains of HCV. The NCR forms a stable secondary structure (Brown et al., *Nucl Acids Res*, 20:5041–5045, 1992), and provides an internal ribosomal entry site (IRES) which is essential for efficient cap-independent viral translation (Wakita and Wands, *J Biol Chem*, 269:14205–1421, 1994).

HCV is the major causative agent of post-transfusion hepatitis (Kuo et al., Science 244:362–364, 1989). Persistent HCV infection often leads to chronic hepatitis, cirrhosis, and hepatocellular carcinoma (Kiyosawa et al., Hepatol. 12:671–675, 1990). Interferon alpha is widely used as an antiviral agent for treatment of chronic HCV infection but its effects have often been found to be limited and transient. (Hoofnagle et al., N. Engl. J. Med. 315:1575–1578, 1986; Yoshioka et al., Hepatol. 16:293–299, 1992). Thus, a need exists for an effective agent for treating HCV infection.

SUMMARY OF THE INVENTION

The invention features a method for inhibiting translation of HCV RNA. In this method, HCV RNA is contacted with an oligonucleotide that is substantially complementary to a portion of the HCV RNA, and contains a nucleotide sequence selected from the group consisting of SEQ ID NOs: 1–28 and 39–43. An oligonucleotide is described herein as being "substantially complementary" or "antisense" to a given nucleic acid, if it is capable of hybridizing to the nucleic acid under physiological conditions. The oligonucleotide used in the method of the invention is preferably between about 10 and about 400 nucleotides in length, more preferably is less than about 250 nucleotides in length, more preferably is less than about 100 nucleotides in length, more preferably is less than about 50 nucleotides in length, and most preferably is between about 12 and about 28 nucleotides in length. The oligonucleotide can be made of DNA, RNA, or any modifications or combinations thereof that preserve the oligonucleotide's ability to hybridize to its complement. For example, the oligonucleotide can be an oligodeoxynucleotide, an oligoribonucleotide, a phosphorothioate oligonucleotide, or a methylphosphonate oligonucleotide, or can contain any combination of these, and other, types of nucleotides and/or inter-nucleotide linkages. A "phosphorothioate oligonucleotide" is defined as an oligonucleotide containing one or more phosphorothioate inter-nucleotide linkages, while a "methylphosphonate oligonucleotide" is defined as an oligonucleotide containing one or more methylphosphonate inter-nucleotide linkages. In both of these types of oligonucleotides, the modified inter-nucleotide linkages can be present in specific regions of the oligonucleotide, e.g., the 5' and/or 3' ends; can be present in random positions within the oligonucleotide; or can be present throughout the oligonucleotide. It is understood that when the oligonucleotide of the invention is a ribonucleotide, "T" in each of the sequences set forth herein represents "U". An "ODN", as used herein, is an oligodeoxynucleotide. An "antisense RNA", as used herein, is an antisense oligoribonucleotide.

In a preferred embodiment, the oligonucleotide contains or consists of a nucleotide sequence selected from the group consisting of SEQ ID NOs: 2, 6, 7, 14, 16, 17, 20, and 23–26. In another embodiment, the oligonucleotide contains or consists of a nucleotide sequence selected from the group consisting of SEQ ID NOs: 1, 3, 5, 8–13, 15, 18, 19, 21, 22, 27, and 28. In another embodiment, the oligonucleotide contains or consists of a nucleotide sequence selected from the group consisting of SEQ ID NOs: 39, 40, 41, 42, and 43.

The method of the invention can be used to inhibit translation of types I, II, III, IV, and V HCV RNA, or of any one of the HCV types described by Simmonds et al., supra. The method can be carried out in vivo, ex vivo, or in vitro. The HCV RNA can be in an animal cell, e.g., an hepatocyte, which can be from a mammal, e.g., a human or a chimpanzee. In a preferred embodiment, the oligonucleotide and the HCV RNA are contacted with one another in a cell (e.g., a human hepatocyte, or a chimpanzee hepatocyte) by introducing into the cell a vector, e.g., an adenovirus vector, containing a sequence which is transcribed in the cell to produce the oligonucleotide as an oligoribonucleotide.

In another aspect, the invention features a vector containing a nucleotide sequence which is transcribed in an animal cell to generate the oligonucleotide of the invention as an oligoribonucleotide. Preferably, the transcribed nucleotide sequence is operably linked to transcription control sequences that function in hepatocytes. Transcription control sequences can include a transcriptional promoter and/or enhancer, and sequences which control the termination of transcription. Transcription control sequences and a transcribed nucleotide sequence are described herein to be "operably linked" if the transcription control sequences control transcription of the transcribed nucleotide sequence. Transcription control sequences that can be used in the vectors of the invention include, but are not limited to, hepatocyte-specific promoters, e.g., the albumin, alpha-fetoprotein, alpha-1-antitrypsin, retinol-binding protein, and asialoglycoprotein receptor promoters. Viral promoters and enhancers, such as those from cytomegalovirus, herpes simplex viruses (types I and II), hepatitis viruses (A, B, and C), and Rous sarcoma virus (RSV; Fang et al., Hepatology 10:781–787, 1989), may also be used in the invention. A "vector" is defined as a replicable nucleic acid construct. Vectors of the invention include, but are not limited to, plasmid vectors and viral vectors. Preferred viral vectors of the invention include, but are not limited to, those derived from replication-defective hepatitis viruses (e.g., HBV and HCV), retroviruses, adenovirus, adeno-associated virus, replication defective herpes simplex viruses, and any modified versions of these vectors.

In another aspect, the invention features a therapeutic composition that can be used in methods of treating or preventing HCV infection. The therapeutic composition contains the oligonucleotide of the invention in a pharmaceutically acceptable carrier, e.g., physiological saline. In a related aspect, the invention features a therapeutic composition containing a vector which contains a nucleotide sequence that is transcribed in an animal cell to generate an oligonucleotide of the invention as an oligoribonucleotide, in a pharmaceutically acceptable carrier.

In other aspects the invention features monoclonal antibodies which are specific for HCV or an HCV-encoded protein, e.g., the monoclonal antibodies (MABs) designated C7-50, C8-59, and C8-48. In a related aspect, the invention includes a method of detecting HCV or an HCV-encoded protein, involving use of one of the MABs C7-50, C8-59, or C8-48 as a reagent for detecting HCV or an HCV-encoded protein. Preferably, the method involves contacting a biological sample with a C7-50, C8-59, or C8-48 monoclonal antibody, and determining whether the monoclonal antibody binds specifically to (i.e., forms an immune complex with) the sample, binding of the monoclonal antibody to the sample indicating the presence of a protein encoded by HCV. The term "biological sample" contemplates a portion of organic material, in solid or liquid form, derived from an in vitro transcription or translation system, from a cell, from an animal, or from a human patient, or from any form of biological specimen in which one skilled in the art desires to determine the presence or absence of HCV or an HCV-encoded protein. The method of detection can be qualitative or quantitative.

Other features and advantages of the invention will be apparent from the following detailed description, the drawings, and the claims.

BRIEF DESCRIPTION OF THE DRAWINGS

FIGS. 13(A–D) is a series of four photographic images of the amount of HCV core protein expressed by HuH-7 cells detected with C7-50 antibody tagged with a fluorescent marker.

FIG. 14 is a photograph of an autoradiographic image of a SDS-polyacrylamide gel showing the inhibitory effect of phosphorothioate (PT) modified A367 antisense ODN on HCV core expression within the cell.

FIG. 15 is an illustration of the positive strand HCV genome SEQ ID NO: 45. Sequences of antisense oligonucleotides of the invention are complementary to the sequence shown.

DETAILED DESCRIPTION

Figure 1:
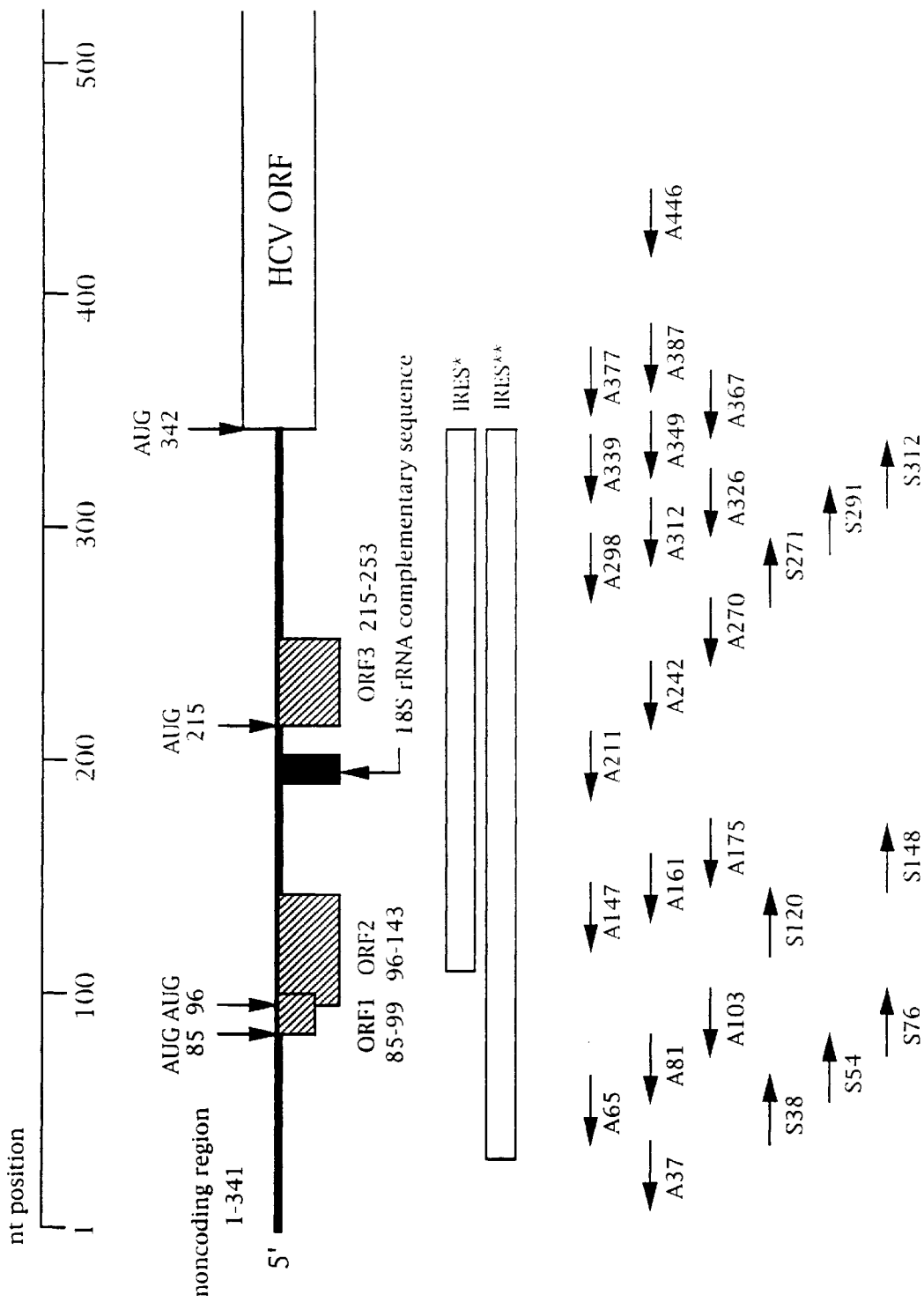
FIG. 1 is a schematic representation of the structure and organization of the 5' region of the HCV genome. The locations of the 4 AUG codons are indicated by downward-pointing arrows. Three small open reading frames (ORFs 1–3) are represented by the boxes containing oblique lines, while the ORF encoding the core protein is indicated by the large open box. The 18S rRNA complementary sequence is located between ORFs 2 and 3 (Brown et al., Nucl. Acids Res. 20:5041–5045, 1992), and is indicated by the black box. Two IRES regions have been reported to be present in the 5' NCR, and are indicated by the smaller open boxes (Tsukiyama-Kohara et al., J. Virol. 66:1476–1483, 1992; Wang et al., J. Virol. 67:3338–3344, 1993). The overlapping oligonucleotides of the invention cover the entire 5' NCR and 5' end of the HCV core coding region. The horizontal arrows represent the sense and antisense oligonucleotides used in this study. The arrowheads indicate the 3' ends of the oligonucleotides.

The antisense oligonucleotides of the invention can be used in methods for inhibiting HCV RNA translation. The antisense oligonucleotides of the invention can be comprised of DNA, RNA, or any modifications or combinations thereof. As an example of the modifications that the oligonucleotides may contain, inter-nucleotide linkages other than phosphodiester bonds, such as phosphorothioate, methylphosphonate, methylphosphodiester, phosphorodithioate, phosphoramidate, phosphotriester, or phosphate ester linkages (Uhlman et al., Chem. Rev. 90(4) :544–584, 1990; Anticancer Research 10:1169, 1990), may be present in the oligonucleotides, resulting in their increased stability. Oligonucleotide stability may also be increased by incorporating 3'-deoxythymidine or 2'-substituted nucleotides (substituted with, e.g., alkyl groups) into the oligonucleotides during synthesis, by providing the oligonucleotides as phenylisourea derivatives, or by having other molecules, such as aminoacridine or poly-lysine, linked to the 3' ends of the oligonucleotides (see, e.g., Anticancer Research 10:1169–1182, 1990). Modifications of the RNA and/or DNA nucleotides comprising the oligonucleotides of the invention may be present throughout the oligonucleotide, or in selected regions of the oligonucleotide, e.g., the 5' and/or 3' ends. The antisense oligonucleotides may also be modified so as to increase their ability to penetrate the target tissue by, e.g., coupling the oligonucleotides to lipophilic compounds. The antisense oligonucleotides of the invention can be made by any method known in the art, including standard chemical synthesis, ligation of constituent oligonucleotides, and transcription of DNA encoding the oligonucleotides, as described below.

Hepatocytes are susceptible to HCV infection, and thus are the preferred cellular targets for the antisense oligonucleotides of the invention. Targeting of antisense oligonucleotides to hepatocytes may be achieved by coupling the oligonucleotides to ligands of hepatocyte-specific receptors. For example, the oligonucleotides can be coupled to asialo-orosomucoid, (poly)L-lysine-asialo-orosomucoid, or any other ligands of the hepatic asialoglycoprotein receptor (Spiess, Biochemistry 29(43):10009–10018, 1990; Wu et al., J. Biol. Chem. 267(18):12436–12439, 1992; Wu et al., Biotherapy 3:87–95, 1991). Similarly, antisense oligonucleotides may be targeted to hepatocytes by being conjugated to monoclonal antibodies that specifically bind to hepatocyte-specific receptors. Antisense oligonucleotides may also be targeted to hepatocytes using specific vectors, as described below.

The antisense oligonucleotides of the invention may be provided exogenously to a target hepatocyte. Alternatively, an antisense RNA may be produced within the target cell by transcription of a nucleic acid molecule comprising a promoter sequence operably linked to a sequence encoding the antisense RNA. In this method, the nucleic acid molecule is contained within a non-replicating linear or circular DNA or RNA molecule, is contained within an autonomously replicating plasmid or viral vector, or is integrated into the host genome. Any vector that can transfect a hepatocyte may be used in the methods of the invention. Preferred vectors are viral vectors, including those derived from replication-defective hepatitis viruses (e.g., HBV and HCV), retroviruses (see, e.g., WO89/07136; Rosenberg et al., N. Eng. J. Med. 323(9):570–578, 1990), adenovirus (see, e.g., Morsey et al., J. Cell. Biochem., Supp. 17E, 1993; Graham et al., in Murray, ed., *Methods in Molecular Biology: Gene Transfer and Expression Protocols*. Vol. 7, Clifton, N.J.: the Human Press 1991: 109–128), adeno-associated virus (Kotin et al., Proc. Natl. Acad. Sci. USA 87:2211–2215, 1990), replication defective herpes simplex viruses (HSV; Lu et al., Abstract, page 66, Abstracts of the Meeting on Gene Therapy, Sep. 22–26, 1992, Cold Spring Harbor Laboratory, Cold Spring Harbor, N.Y.), and any modified versions of these vectors. Methods for constructing expression vectors are well known in the art (see, e.g., Molecular Cloning: A Laboratory Manual, Sambrook et al., eds., Cold Spring Harbor Laboratory, 2nd Edition, Cold Spring Harbor, N.Y., 1989).

Appropriate regulatory sequences can be inserted into the vectors of the invention using methods known to those skilled in the art, for example, by homologous recombination (Graham et al., J. Gen. Virol. 36:59–72, 1977), or other appropriate methods (Molecular Cloning: A Laboratory Manual, Sambrook et al., eds., Cold Spring Harbor Laboratory, 2nd Edition, Cold Spring Harbor, N.Y., 1989). Promoters are inserted into the vectors so that they are operably linked 5' to the nucleic acid sequence encoding the antisense oligonucleotide. Any promoter that is capable of directing initiation of transcription in a eukaryotic cell may be used in the invention. For example, non-tissue specific promoters, such as the cytomegalovirus (DeBernardi et al., Proc. Natl. Acad. Sci. USA 88:9257–9261, 1991, and references therein), mouse metallothionine I gene (Hammer, et al., J. Mol. Appl. Gen. 1:273–288, 1982), HSV thymidine kinase (McKnight, Cell 31:355–365 1982), and SV40 early (Benoist et al., Nature 290:304–310, 1981) promoters may be used. Non-tissue specific promoters may be used in the invention, as expression of antisense HCV oligonucleotides in non-liver cells directed by the non-tissue specific promoters should be harmless to the non-liver cells, because of the specificity of the antisense oligonucleotides of the invention for viral sequences. However, preferred promoters for use in the invention are hepatocyte-specific promoters, the use of which ensures that the antisense oligonucleotides are expressed primarily in hepatocytes. Preferred hepatocyte-specific promoters include, but are not limited to the albumin, alpha-fetoprotein, alpha-1-antitrypsin, retinol-binding protein, and asialoglycoprotein receptor promoters. Viral promoters and enhancers, such as those from cytomegalovirus, herpes simplex viruses (types I and II), hepatitis viruses (A, B, and C), and Rous sarcoma virus (RSV; Fang et al., Hepatology 10:781–787, 1989), may also be used in the invention.

The antisense oligonucleotides of the invention, and the recombinant vectors containing nucleic acid sequences encoding them, may be used in therapeutic compositions for preventing or treating HCV infection. The therapeutic applications of antisense oligonucleotides in general are described, e.g., in the following review articles: LeDoan et al., Bull. Cancer 76:849–852, 1989; Dolnick, Biochem. Pharmacol. 40:671–675, 1990; Crooke, Annu. Rev. Pharmacol. Toxicol. 32, 329–376, 1992. The therapeutic compositions of the invention may be used alone or in admixture, or in chemical combination, with one or more materials, including other antisense oligonucleotides or recombinant vectors, materials that increase the biological stability of the oligonucleotides or the recombinant vectors, or materials that increase the ability of the therapeutic compositions to penetrate hepatocytes selectively. The therapeutic compositions of the invention may be administered in pharmaceutically acceptable carriers (e.g., physiological saline), which are selected on the basis of the mode and route of administration, and standard pharmaceutical practice. Suitable pharmaceutical carriers, as well as pharmaceutical necessities for use in pharmaceutical formulations, are described in *Remington's Pharmaceutical Sciences*, a standard reference text in this field, and in the USP/NF.

The therapeutic compositions of the invention can be administered in dosages determined to be appropriate by one skilled in the art. An appropriate dosage is one which effects a reduction in the disease caused by HCV infection, and/or one which is effective at preventing HCV infection. It is expected that the dosages will vary, depending upon the pharmacokinetic and pharmacodynamic characteristics of the particular agent, and its mode and route of administration, as well as the age, weight, and health (including renal and hepatic function) of the recipient; the nature and extent of the disease; the frequency and duration of the treatment; the type of, if any, concurrent therapy; and the desired effect. It is expected that a useful dosage contains between about 0.1 to 100 mg of active ingredient per kilogram of body weight. Ordinarily, 0.5 to 50 mg, and preferably, 1 to 10 mg of active ingredient per kilogram of body weight per day given in divided doses, or in sustained release form, is appropriate.

The therapeutic compositions of the invention may be administered to a patient by any appropriate mode, e.g., parenterally, intraperitoneally, or intravenously, as determined by one skilled in the art. Alternatively, it may by necessary to administer the treatment surgically to the target tissue. The treatments of the invention may be repeated as needed, as determined by one skilled in the art.

The invention also includes any other methods which accomplish in vivo transfer of nucleic acids into eukaryotic cells. For example, the nucleic acids may be packaged into liposomes, non-viral nucleic acid-based vectors, erythrocyte ghosts, or microspheres (microparticles; see, e.g., U.S. Pat. No. 4,789,734; U.S. Pat. No. 4,925,673; U.S. Pat. No. 3,625,214; Gregoriadis, Drug Carriers in Biology and Medicine, pp. 287–341 (Academic Press, 1979)). Further, delivery of antisense oligonucleotides may be accomplished by direct injection of the oligonucleotides into target tissues, for example, in a calcium phosphate precipitate or coupled with lipids.

EXPERIMENTAL DATA

EXAMPLE I

Synthetic Oligodeoxynucleotides (ODNs)

A. Materials and Methods

Construction and Expression of HCV cDNAs:

HCV cDNAs (nucleotide positions 1 to 1321) were isolated from anti-HCV positive sera taken from two Japanese individuals (TH and NT; kindly provided by Dr. Shinichi Kakumu, Nagoya University, Japan) using the polymerase chain reaction (PCR), as described (Yoshioka et al., Hepatol. 16:293–299, 1992). Amplified cDNA fragments were inserted into the pUC19 cloning vector. The nucleotide sequences of 3 clones obtained from each individual were determined by the di-deoxy chain termination sequencing method. The clones exhibited 0.3 to 0.6% nucleotide sequence variation within the same individual, and 21.6 to 21.9% nucleotide sequence variation between the two individuals. Clones from TH exhibited 94.2 to 95.1% nucleotide sequence homology to HCV-BK (Takamizawa et al., J. Virol. 65:1105–1113, 1991) and HCV-J (Kato et al., Proc. Natl. Acad. Sci. USA 87:9524–9528, 1990), which are type II HCV clones. One clone from TH, designated 2-2, was selected for further analysis. Clones from NT exhibited 94.2 to 94.5% nucleotide sequence homology to HCV-J6, which is a type III HCV clone (Okamoto et al., J. Gen. Virol. 72:2697–2704, 1991). A clone designated 4-1 was selected from patient NT for further study. Bacteriophage T7 promoter sequences were inserted upstream of the 5' ends of the HCV inserts (FIG. 2), and the resulting expression vectors, designated pTH for the type II HCV genotype, and pNT for the type III HCV genotype, were used for further experiments.

Figure 4:
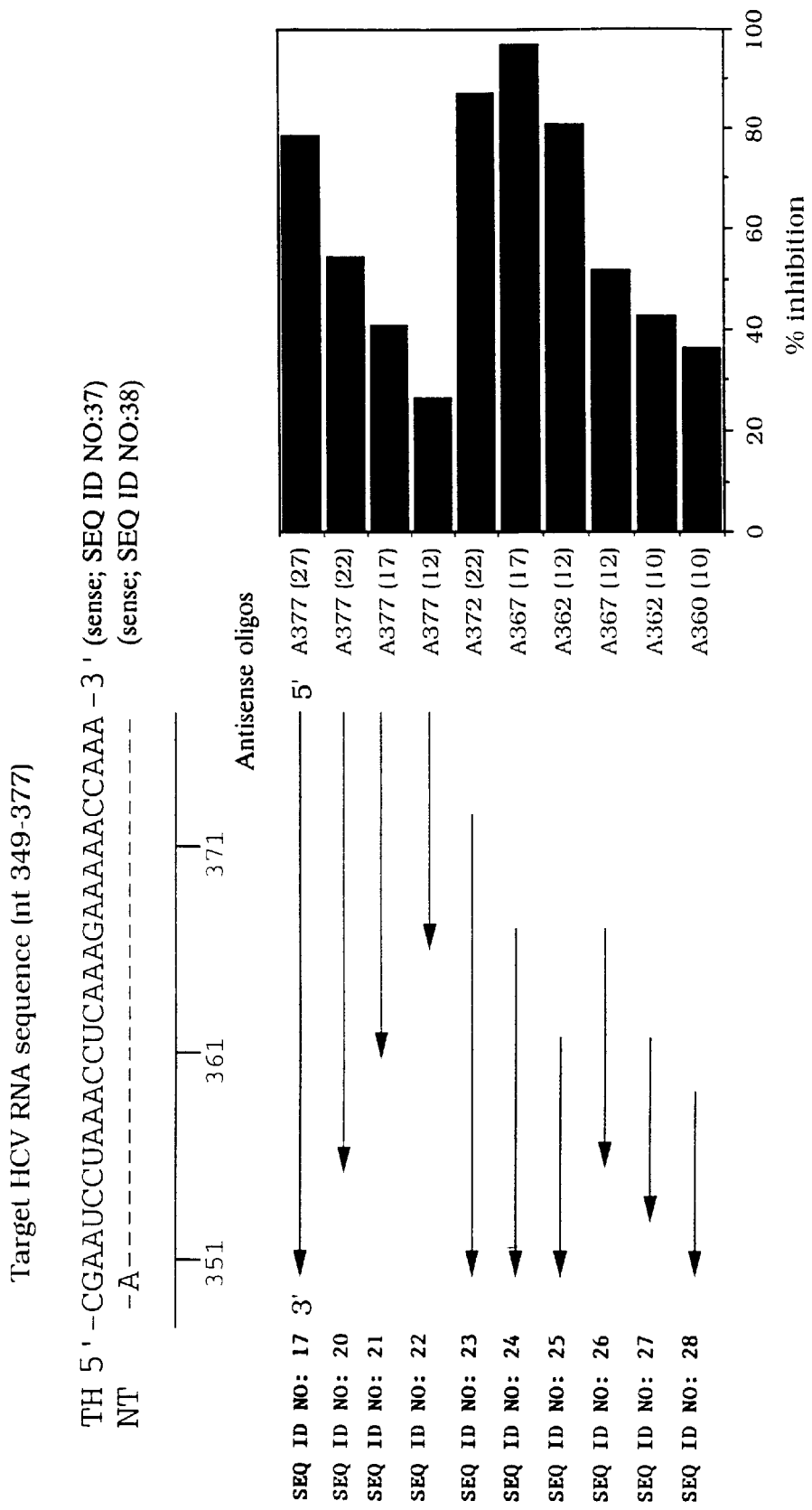
FIG. 4 is a graph showing the results of fine sequence analysis of antisense ODN effects in the A377 (SEQ ID NO: 17)-defined region of HCV RNA. The numbers after the "A"s indicate the corresponding HCV genomic positions of the 5' ends of the ODNs, and the numbers in parentheses indicate the lengths of the ODNs. The positions and sequence specificities of the ODNs are illustrated on the left. The arrowheads indicate the 3' ends of the ODNs. Percent inhibition of HCV type II RNA translation by each of the indicated ODNs is shown on the right.

Design and Synthesis of Oligodeoxynucleotides:

A series of sense and antisense ODNs were synthesized based on the sequence of pTH type II HCV by standard phosphoramidite chemistry using a Milligen/Biosearch 8750 synthesizer. The ODNs were purified after NH₄OH detachment 55° C. (6 hours) and NAP 25 column (Pharmacia, Piscataway, N.J.) desalting with 0.1 M NaHCO₃ by reverse phase HPLC (Tritylon, TEAA 0.1 M pH 7.25) and an acetonitrile gradient. The ODNs were lyophilized, de-blocked with 1 M acetic acid for 1 hour, neutralized with TEA, passed through a NAP 10 column, and lyophilized to dryness. The HCV nucleotide positions to which the ODNs used in this study correspond are shown in FIG. 1. In combination, the antisense ODNs are complementary to the entire HCV 5' NCR, and part of the HCV core region. The number given to each ODN indicates the position on the HCV genomic map to which the 5' end of the ODN corresponds. The numbers in parentheses, as shown in FIG. 4, indicate the lengths of the ODNs. The sizes and G-C contents of the ODNs are shown in Table I. The molar concentrations of the ODNs used in the experiments were adjusted according to sequence lengths.

In vitro Transcription and Translation of HCV RNA:

pTH and pNT were linearized using HindIII, digested with proteinase K, extracted with phenol/chloroform, and precipitated in ethanol, prior to in vitro transcription. Transcription reactions were carried out using T7 RNA polymerase (Promega, Madison, Wis.), and the resulting transcripts were purified by urea-polyacrylamide gel electrophoresis (urea-PAGE), followed by precipitation in ethanol. RNA transcripts were labeled with [α-$^{33}$P]UTP (New England Nuclear, Billerica, Mass.) during the transcription reactions, as required. Type II HCV RNA was used in this study, unless otherwise indicated.

One µg of HCV RNA was mixed with a 10-fold molar excess of sense or antisense ODN, or with distilled water. The mixtures were heated at 70° C. for 5 minutes, and then at 50° C. for 10 minutes, followed by incubation at room temperature for 10 minutes, in order to complete annealing of target HCV RNA and the ODN. In some experiments, the annealing step was omitted. HCV RNA incubated in the absence of ODN, and rabbit reticulocyte lysate incubated without HCV RNA, were used as controls. In vitro translation reactions were carried out as described (Pelham et al., Eur. J. Biochem. 67:247–256, 1976), with minor modifications. Rabbit reticulocyte lysates (Promega, Madison, Wis.) were added to HCV RNA, or HCV RNA-ODN hybrids, to a final volume of 25 µl in the presence of [$^{35}$S]-methionine (New England Nuclear, Billerica, Mass.). After incubation at 30° C. for 1 hour, 4 µl of each of the reaction mixtures were analyzed by sodium dodecyl sulfate-polyacrylamide gel electrophoresis (SDS-PAGE). The gels were dried, and exposed to X-ray film, and the developed films were analyzed by densitometric scanning.

Two µl of each reaction mixture were precipitated with TCA. The specific incorporation of radioactivity into the translated protein products was determined using a liquid scintillation counter (Pelham et al., Eur. J. Biochem. 67:247–256, 1976). Typically, between 500–5000 cpm/µl were detected in the translated protein products. Background counts were around 500 cpm/µl in the control mixture containing no HCV RNA. The amounts of HCV core envelope fusion protein produced in control reactions were used as standards, and the amounts of HCV protein synthesized in the presence of the ODNs were compared after subtraction of background counts. The percent inhibition of HCV RNA translation by each ODN was calculated using this data.

cDNA Synthesis from HCV RNA:

ODNs A65, A103, A377, and A387 (SEQ ID NOs: 2, 4, 17, and 18, respectively) were end-labeled with [γ$^{33}$P]-ATP (New England Nuclear, Billerica, Mass.) using T4 polynucleotide kinase (Promega, Madison, Wis.). Specific incorporation of radioactivity into the ODN was determined after purification through a Sephadex G-25 spin column (Boehringer Mannheim, Germany). The specific activity of each ODN was normalized by adding an appropriate amount of unlabeled ODN. The labeled ODNs were hybridized with HCV RNA under the same conditions as described above for the in vitro translation reactions, and the cDNAs were synthesized by adding Moloney Murine Leukemia Virus reverse transcriptase (Gibco BRL, Gaithersburg, Md.). An aliquot of each reaction mixture was fractionated by denaturing urea-PAGE. The gel was dried, and the products were visualized using autoradiography.

HCV RNA Stability:

ODNs A377 (SEQ ID NO: 17) and A387 (SEQ ID NO: 18) were hybridized with [α-$^{33}$P]-labeled HCV RNA, incubated under the same conditions as described above, and added to rabbit reticulocyte lysate in order to determine the level of RNaseII activity present in the in vitro translation reactions. After an incubation at 30° C. for 15 minutes, the RNA was extracted (Chomczynski et al., Anal. Biochem. 162:156–159, 1987), and aliquots of the extracted RNA were analyzed by denaturing urea-PAGE.

B. RESULTS

Figure 2A:
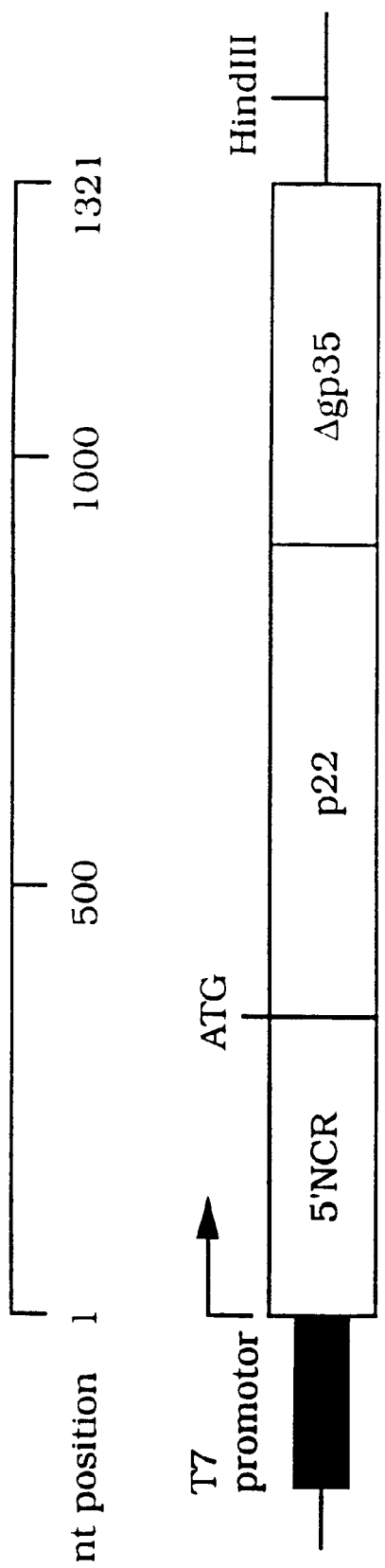
FIG. 2A is a schematic representation of the structural organization of the vector used to express HCV RNA in this study. A T7 promoter and either HCV type II, or HCV type III, cDNA sequences (nucleotide positions 1 to 1321, or 2 to 1321, respectively) were inserted into the pUC19 vector. The numbers represent the corresponding nucleotide positions of HCV cDNA. The AUG codon of the HCV core open reading frame is indicated. P22 is a putative HCV nucleocapsid protein, and gp35 is one of the putative HCV envelope proteins (Hijikata et al., Proc. Natl. Acad. Sci. USA 88:5547–5551, 1991).
Figures 2B, 3A, 3B:
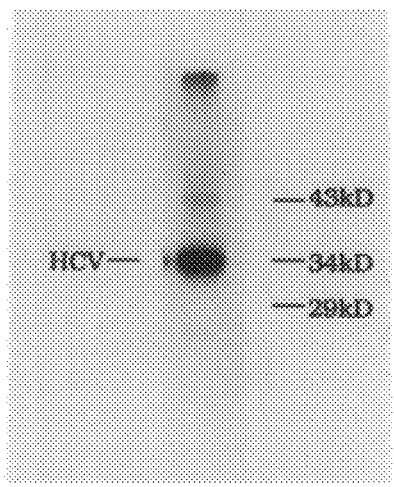
FIG. 2B is an autoradiogram of the in vitro translation products of type II HCV RNA, fractionated by SDS-PAGE. The primary core-envelope protein product migrates at approximately 34 kilo-Daltons (kD), as indicated.
FIG. 3A is a table showing the dose-dependent inhibition of HCV RNA translation by antisense ODNs A161 (SEQ ID NO: 6). Sense ODN S120 (SEQ ID NO: 32) was used in this experiment as a negative control. The ODNs were added to the reactions at molar ratios varying from 1:1 to 100:1, with respect to template HCV RNA. Percent inhibition of protein synthesis by the two ODNs is indicated.
FIG. 3B is a table showing the effects of HCV antisense ODN A161 (SEQ ID NO: 6) and sense ODN S120 (SEQ ID NO: 32) on luciferase mRNA translation.

In vitro Translation of HCV Protein:

A cell free in vitro translation system was used to express the HCV core envelope fusion protein, and to determine whether antisense ODNs are capable of inhibiting HCV RNA translation. The expression vector used in these experiments contains the complete HCV 5' NCR, and a structural coding region containing the entire core and part of the envelope region of type II and type III HCV cDNAs (FIG. 2). The RNA transcribed from this vector contains 980 nucleotides of HCV coding region. The in vitro translated product from type II HCV RNA fractionates as a 34 kD protein by electrophoresis (FIG. 2). That the in vitro translated protein product is related to HCV, was confirmed by immunoprecipitation with polyclonal anti-HCV antibodies and monoclonal antibodies raised against recombinant HCV core protein.

Inhibition of HCV RNA Translation by Antisense Oligodeoxynucleotides:

A series of antisense and sense ODNs corresponding to the HCV 5' NCR were analyzed for their effects on in vitro translation of HCV RNA (FIG. 1). These experiments were performed in duplicate, and repeated at least twice for each oligonucleotide shown in FIG. 1. HCV RNA was incubated in a rabbit reticulocyte lysate system after hybridization with each ODN, and the amount of protein produced in these reactions was determined by measuring the levels of radioactivity incorporated into the core envelope fusion protein. Further quantitation was carried out by densitometric scanning of exposed X-ray films. Table I summarizes the results of these analyses, showing the effects of each ODN on translation of both type II and type III HCV RNA. Sense ODNs either inhibited HCV RNA translation only very weakly, or actually stimulated HCV protein synthesis, compared to reactions lacking ODNs. In contrast, most of the antisense ODNs inhibited HCV RNA translation to significant levels, compared to reactions lacking ODNs. For example, six antisense ODNs, A65, A161, A175, A339, A367, and A377 (SEQ ID NOs: 2, 6, 7, 14, 16, and 17, respectively), exhibited more than 50% inhibition of both type II and type III HCV RNA translation. The target sequence of A161 (SEQ ID NO: 6) is in a highly conserved domain in the HCV 5' NCR. However, other antisense ODNs that overlap with this region of HCV RNA exhibited significantly less inhibition of HCV RNA translation than A161. For example, A147 (SEQ ID NO: 5) demonstrated only 20.4% inhibition. A367 (SEQ ID NO: 16), which is complementary to the initiation codon and HCV core coding region, showed the highest level of inhibition of HCV RNA translation (97.6%) of the ODNs tested. ODNs A367 (SEQ ID NO: 16) and A377 (SEQ ID NO: 17), which overlap with one another over a 17 nucleotide-long region, both showed a substantial inhibition of both type II and type III HCV core protein synthesis, even though the pNT HCV type III RNA has a one nucleotide mutation or mismatch when compared to the A367 (SEQ ID NO: 16) ODN target sequence. However, other overlapping ODNs in this region, as illustrated by ODNs A349 (SEQ ID NO: 15) and A387 (SEQ ID NO: 18), demonstrated only minor inhibitory effects, even though A349 (SEQ ID NO: 15) is complementary to the core AUG start codon. Another HCV core coding region antisense ODN, A446 (SEQ ID NO: 19), also showed weak inhibitory effects. Taken together, these results indicate that the sequence immediately downstream from the first AUG codon of the HCV core open reading frame is a good target sequence for antisense oligonucleotide inhibition of HCV RNA translation. A65 (SEQ ID NO: 2) also inhibited HCV RNA translation to a substantial degree, even though the region of HCV RNA that this ODN corresponds to is far upstream from the initiation codon. It is of interest that ODN A211 (SEQ ID NO: 8) binds to a putative 18S rRNA complementary sequence (Brown et al., Nucl. Acids Res. 20:5041–5045, 1992), and demonstrated no inhibitory effect for both type II and type III HCV RNA translation. The G-C contents and $T_m$s of the various ODNs were not related to the degree of HCV RNA translation inhibition exhibited by the ODNs (Table I).

A dose dependent inhibitory effect on HCV RNA translation was observed using A161 (SEQ ID NO: 6; FIG. 3). At the highest concentration of A161 used (molar ratio of oligo:RNA=100:1), HCV protein synthesis was almost completely blocked. It is noteworthy that even at this high concentration, the sense ODN (S120; SEQ ID NO: 32) had no inhibitory effect on HCV RNA translation. Furthermore, as a control, both of these ODNs were incubated with an unrelated mRNA encoding luciferase. Neither A161 (SEQ ID NO: 6) nor S120 (SEQ ID NO: 32) inhibited luciferase mRNA translation at any concentration employed (FIG. 3). Other antisense ODNs actually were found to stimulate translation of luciferase mRNA (Table II). This observation is reminiscent of the observation that translation of HCV RNA is stimulated by certain sense ODNs (Table I). In summary, certain antisense ODNs inhibit HCV RNA translation in a sequence specific manner in vitro, even though the same ODNs were found to, if anything, increase the level of translation of an unrelated mRNA.

To determine whether annealing of antisense ODNs to target RNA prior to the in vitro translation reaction is required for effective inhibition of translation, translation reactions were carried out without the annealing step. Antisense ODNs were added just prior to the HCV RNA translation step, and the degree of inhibition was determined. In the absence of the annealing step, ODNs showed the same, or higher, levels of inhibition of HCV RNA translation compared to reactions carried out with the annealing step (Table II).

Specific Inhibition of HCV RNA Translation by Short Antisense Oligos in the A377 (SEQ ID NO: 17) Region:

ODNs A367 (SEQ ID NO: 16) and A377 (SEQ ID NO: 17) were the most effective among those tested as inhibitors of HCV type II and type III RNA translation (Table I). Since there is a mutation at nucleotide position 350 in type III HCV RNA (FIG. 5), and because the sequence complementary to this position is contained within ODN A367, but not in A377, the HCV region defined by ODN A377 (SEQ ID NO: 17) was selected for further study to determine the specific nucleotide sequence requirements for inhibition of HCV RNA translation. Different length ODNs derived from the A377 (SEQ ID NO: 17)-defined region of HCV were tested with type II HCV RNA in the in vitro translation assay. As nucleotides were deleted from the 3' end of the A377 (SEQ ID NO: 17) sequence, the degree of inhibition was reduced in proportion to the size of the deletion. In contrast, deletions from the 5' end of A377 (SEQ ID NO: 17) increased the inhibitory effect from 78.4% (A377; SEQ ID NO: 17; 27 nucleotides) to 96.9% with A367 (SEQ ID NO: 16; 17 nucleotides). It is noteworthy that A362 (SEQ ID NO: 25), which is only 12 nucleotides in length, significantly inhibited HCV RNA translation (by 80.7%). The inhibition of translation was substantially reduced using ODNs of only 10 nucleotides in length, e.g., oligonucleotides A362 (SEQ ID NO: 27) and A360 (SEQ ID NO: 28). These experiments show that the HCV RNA region between nucleotide positions 351–367, which is highly conserved in both type II and type III HCV clones, is an excellent viral RNA target for antisense oligonucleotide inhibition.

Figure 5:
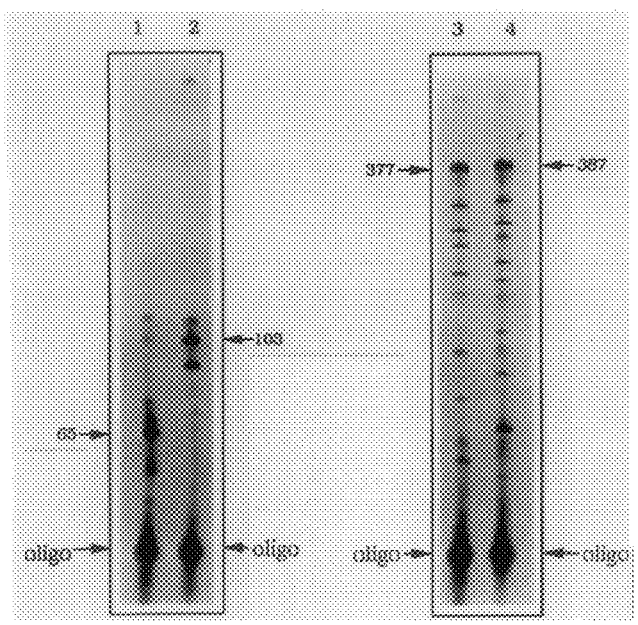
FIG. 5 is an autoradiogram of cDNA synthesis reactions fractionated on a 6% denaturing (urea) polyacrylamide gel. The reactions were carried out using HCV RNA as the template, and ODNs A65 (SEQ ID NO: 2; lane 1), A103 (SEQ ID NO: 4; lane 2), A377 (SEQ ID NO: 17; lane 3), and A387 (SEQ ID NO: 18; lane 4) as primers. The predominate cDNA products are indicated by the numbered arrows, and unextended ODN primers are indicated at the bottom of the gel (ODN).

HCV cDNA Synthesis with Antisense Oligonucleotides:

Both the binding efficiencies and the nucleotide sequence specificities of the various antisense ODNs may play roles in determining the degree of inhibition of HCV RNA translation they exhibit. To determine the relative binding affinities of different antisense ODNs to HCV RNA, cDNA synthesis assays were carried out. ODNs A65 (SEQ ID NO: 2) and A377 (SEQ ID NO: 17), which inhibit HCV RNA translation, and ODNs A103 (SEQ ID NO: 4) and A387 (SEQ ID NO: 18), which are derived from the same general regions of the HCV genome as ODNs A65 (SEQ ID NO: 2) and A377 (SEQ ID NO: 17), respectively, but unlike the latter do not inhibit HCV translation, were used in this analysis. The ODNs were labeled with [$\gamma$-$^{33}$P]ATP, and the specific activities were normalized in all experiments. The same ratio of HCV RNA to ODN (1:10) used in the translation assays was used in the cDNA synthesis reactions. FIG. 5 shows the results of these experiments. The predominant cDNA products fractionated at their expected sizes by urea-PAGE. Several smaller bands were detected in lanes 3 and 4 (FIG. 5), and were probably generated in part because of the secondary structure of the template RNA, which blocks elongation of the cDNAs. The patterns of the DNA ladders generated in the reaction containing ODN A377 (SEQ ID NO: 17; FIG. 5, lane 3), which inhibits HCV RNA translation, and the reaction containing ODN A387 (SEQ ID NO: 18; FIG. 5, lane 4), which does not inhibit HCV RNA translation, are nearly identical. These data show that inhibition of HCV RNA translation is not a function of non-specific binding of ODNs to HCV RNA target sequences, but rather, is due to the specificity of the HCV RNA target sequence/antisense ODN interaction. Further, these data show that the differences in inhibition of HCV RNA translation observed using different antisense ODNs is not due to different binding affinities of the ODNs, but rather is due to binding specificity of the ODNs to HCV RNA, as the levels of cDNA products produced in the reactions using different antisense ODNs as primers are similar.

Figure 6:
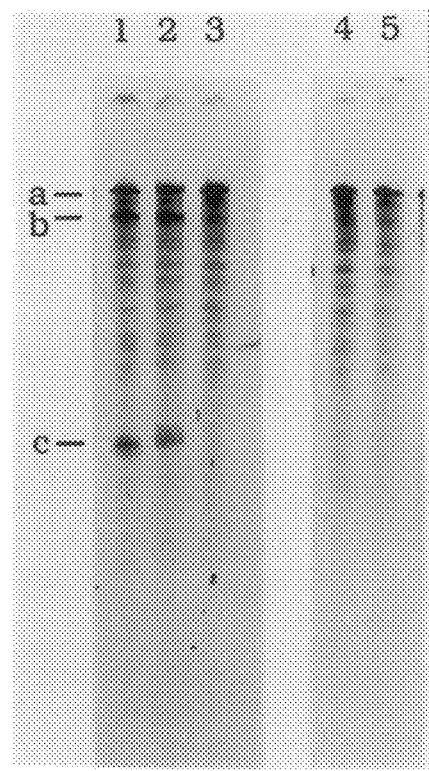
FIG. 6 is an autoradiogram showing the stability of HCV RNA during in vitro translation reactions. [$\alpha$-$^{33}$P] labeled HCV RNAs were incubated with antisense ODNs A377 (SEQ ID NO: 17; lane 1) and A367 (SEQ ID NO: 16; lane 2), sense ODN S120 (SEQ ID NO: 32; lane 3), and no ODN (lanes 4 and 5). The RNA mixtures were incubated with rabbit reticulocyte lysates (lanes 1–4), and then extracted. Lane 5 shows HCV RNA mixed with rabbit reticulocyte lysate, and extracted immediately, without a 15 minute incubation at 30° C. Full length HCV RNA (1300 nucleotides) is indicated by "a", while the cleaved HCV RNA products of approximately 900 and 380 nucleotides are indicated by "b" and "c", respectively.

HCV RNA Stability and the Mechanism of Antisense ODN Effects:

RNase H activity has been proposed to be one of the major mechanisms for the inhibitory effects of antisense oligonucleotides (Uhlmann et al., Chem. Rev. 90(4) :543–584, 1990). To determine the stability of HCV RNA during in vitro translation reactions, [$^{33}$P]-labeled HCV RNA was synthesized and purified by gel electrophoresis. Labeled HCV RNA was hybridized with ODNs, and incubated with rabbit reticulocyte lysates in the translation assay. After 15 minutes of incubation at 30° C., HCV RNA was extracted, and loaded onto gels under denaturing conditions. HCV RNA incubated without any ODN showed the expected full size transcripts, and minor degradation products (FIG. 6, lanes 4 and 5). However, RNAs hybridized with ODNs demonstrated two additional major bands (FIG. 6, lanes 1 and 2). The sizes of the shorter RNA bands are consistent with their corresponding to cleaved products generated by RNase H activity. It is noteworthy that labeled HCV RNAs were not completely degraded under these conditions. Furthermore, similar levels of HCV RNA cleavage were observed for both inhibitory and non-inhibitory oligonucleotides. Thus, it is not likely that RNAse H degradation is the major mechanism whereby the above-described antisense oligonucleotides inhibit HCV RNA translation.

Figures 7A, 7B:
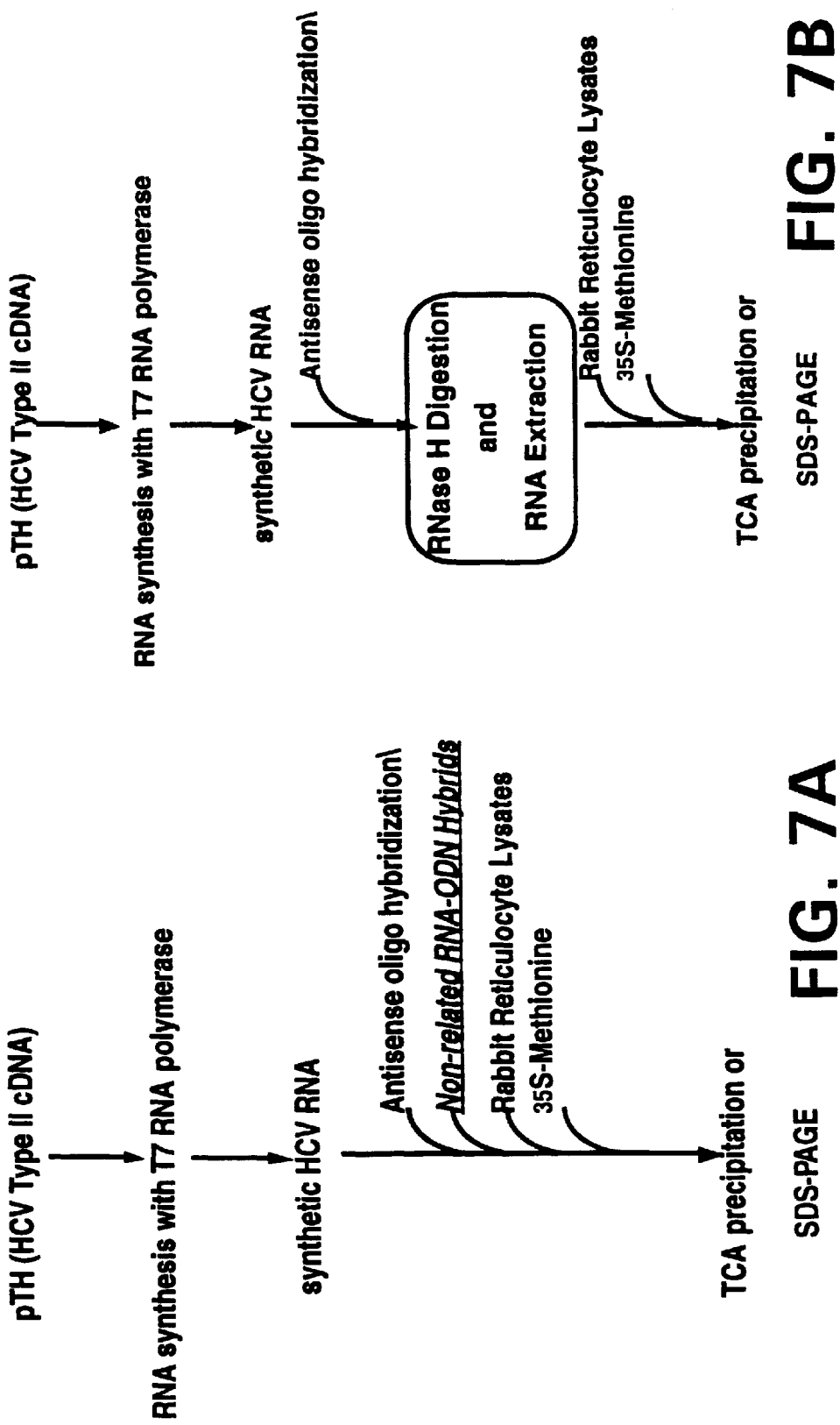
FIGS. 7(A–B) is a schematic diagram showing the experimental procedure for determining whether antisense oligonucleotides inhibit transcription of HCV Type II cDNA by an RNase H dependent or independent mechanism.

To confirm that the primary mechanism of antisense inhibition of HCV translation is not RNase H dependent, the experiment diagrammed in FIG. 7 was performed. Diagram (A) illustrates an RNase H independent inhibition assay, and diagram (B) illustrates an RNase H dependent inhibition assay. Non-related RNA-oligodeoxynucleotide hybrids were employed to remove endogenous RNase H activity from the rabbit reticulocyte lysates.

Figure 8:
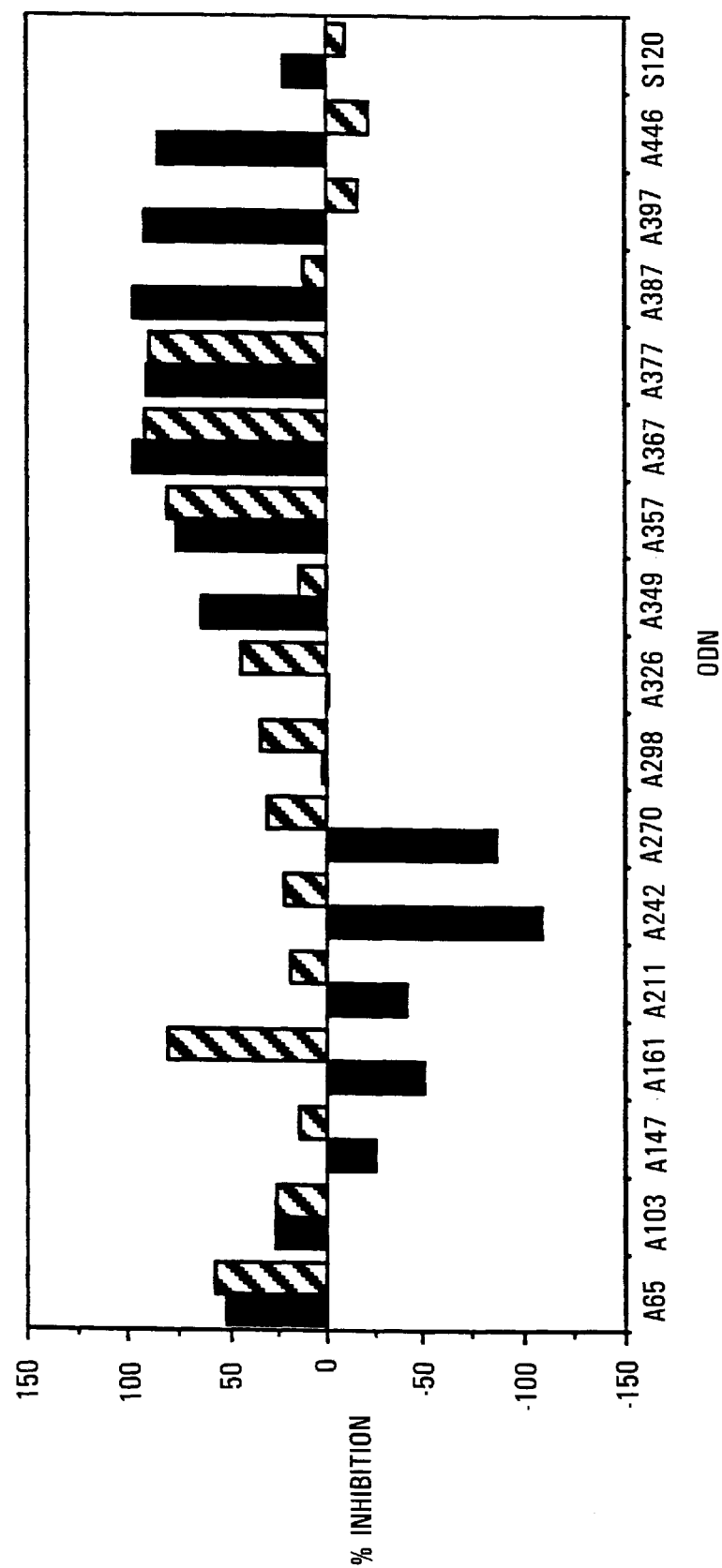
FIG. 8 is a bar graph summarizing the effect of antisense oligonucleotides on HCV mRNA translation, as measured by RNase H dependent (hatched bars) and RNase H independent (solid bars) mechanisms.

The results, summarizing the mechanism of the inhibition shown by the various oligonucleotides of FIG. 1, are shown in FIG. 8. There were three highly restricted domains in the 5' NT and HCV core gene regions which were susceptible to antisense "attack" by a RNase dependent mechanism (hatched bars) as defined by oligonucleotides [A65], [A161] and [A357, A367, A377]. Two other regions appeared susceptible to inhibition by ODNs by a RNase H independent mechanism, as shown by the black bars. Several oligonucleotides using this RNase H independent mechanism were most effective around the ATG of the HCV core gene.

Fine specificity analysis of the HCV RNA region 351–377 revealed that 12 mer A362 retained the capacity to inhibit HCV RNA translation substantially. It is important to note that several ODNs effectively blocked both type I and II HCV RNA translation despite the presence of mutations in the type II clone. Additional studies, as described below, indicate that these ODNs are effective inhibitors of HCV RNA translation using cells stably transfected with HCV, where HCV gene expression is under the control of a tetracycline inducible promoter. These in vitro findings are encouraging since, in vivo, HCV presumably replicates within the cytoplasm, has a very low copy number in hepatocytes, and may be susceptible to antisense oligodeoxynucleotide effects. Thus, by defining critical regions of the HCV genome, it is likely that such ODNs may be used as an approach for antiviral therapy in vivo.

EXAMPLE II

Oligoribonucleotides (Antisense RNA)

Antiviral Effects of Antisense HCV mRNA Constructs:

Antisense RNAs can be transcribed in situ from a DNA vector that is transcribed into the antisense sequence, potentially overcoming any difficulties in transporting an ODN through the extracellular membrane. In order to explore the possible antiviral effects antisense RNA has on HCV mRNA translation, nucleotide sequences transcribed into antisense RNAs were inserted into vectors under the control of the cytomegalovirus promoter.

Figure 9:
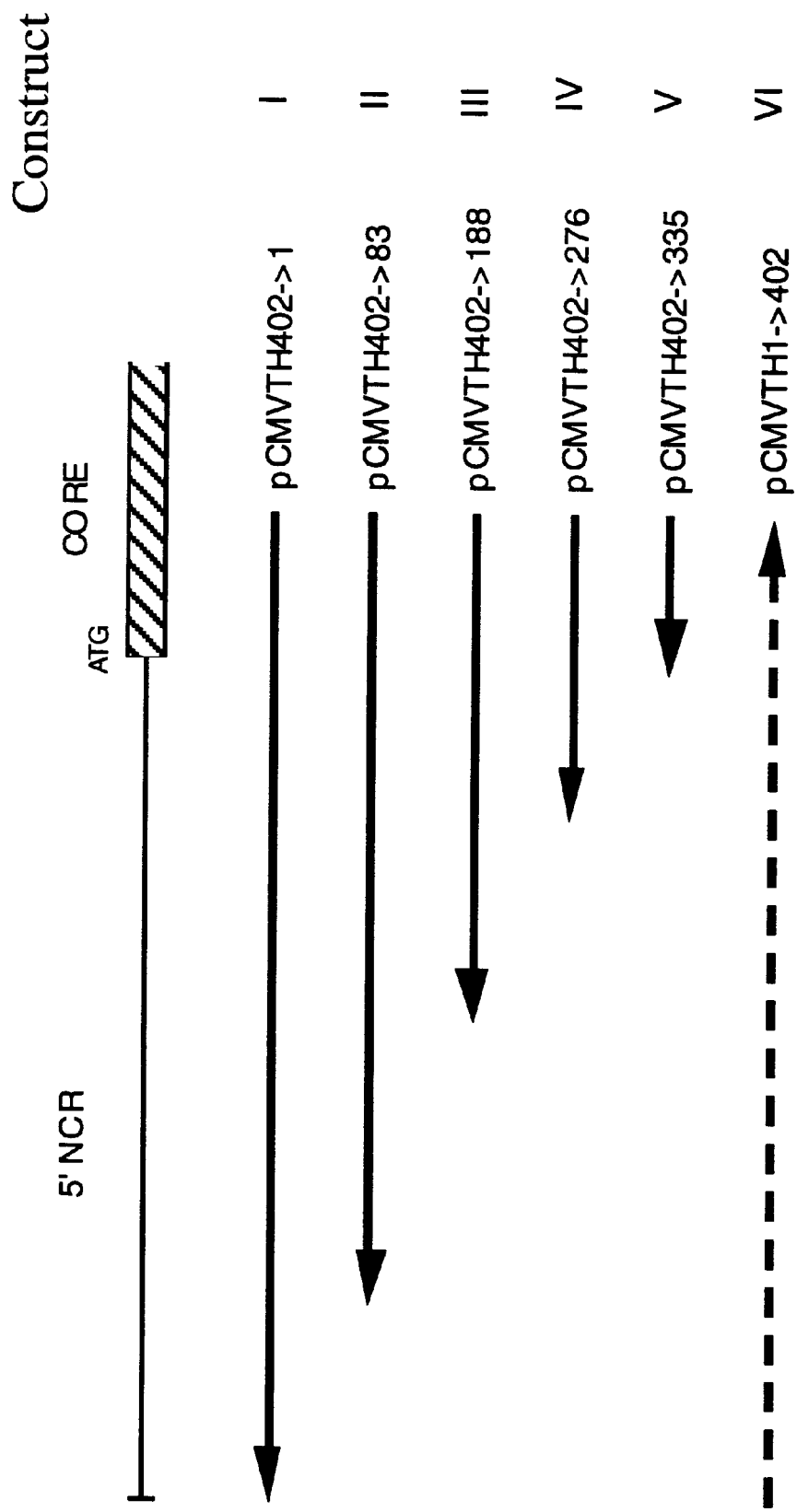
FIG. 9 is a schematic illustration of examples of antisense HCV mRNA-expressing constructs. The pCMVTH1—402 is the control sense construct (dotted line). The numbers refer to the nucleotides of the 5' NCR and core gene.

First, an HCV genotype 1b (II) cDNA fragment containing nucleotides 1 to 402 was amplified from pUCHCVTH (Wakita et al., J Biol Chem, 269:14205–1421, 1994) and XbaI and HindIII restriction enzyme sites were introduced at the 5' and 3' ends, respectively, by polymerase chain reaction. This fragment was introduced in reverse orientation into the HindIII and XbaI sites of pcDNA3 (Invitrogen, San Diego, Calif.) to yield the construct pCMVTH402→1, which is transcribed to produce the antisense RNA (I) (FIG. 9; SEQ ID NO: 39). The polymerase chain reaction fragment was also digested with NcoI (nucleotide position 83), PpuMI (nucleotide position 188), and StuI (nucleotide position 276) and introduced into the HindIII and EcoRV sites of pcDNA3 after blunting where appropriate to yield the constructs pCMVTH402→83 (II) (FIG. 9; SEQ ID NO: 40), pCMVTH402→188 (III) (FIG. 9; SEQ ID NO: 41), and pCMVTH402→276 (IV) (FIG. 9; SEQ ID NO: 42). To construct pCMVTH402→335 (V) (FIG. 9; SEQ ID NO: 43), the corresponding fragment was amplified from PUCHCVTH with introduction of an XbaI restriction site at nucleotide position 335 and introduced into pcDNA3. The control sense construct pCMVTH1→402 (VI) was constructed by digestion of pUCHCVTH with BamHI (nucleotide position 1) and AatII (nucleotide position 402) and insertion of the fragment into the BamHI and EcoRV sites of pcDNA3. A negative control construct was made by introduction of the HindIII-NaeI fragment of pGEM11 into the HindIII-EcoRV sites of pcDNA3; this is transcribed to produce an RNA which is not complementary to HCV. FIG. 15 shows the sequence of HCV. The sequences of antisense RNAs (I), (II), (III), (IV), and (V) are complementary to the sequence shown in FIG. 15, e.g., the sequence of antisense RNA (I)(SEQ ID NO: 39) is the complement of nucleotides 1–402 of FIG. 15.

Figure 10:
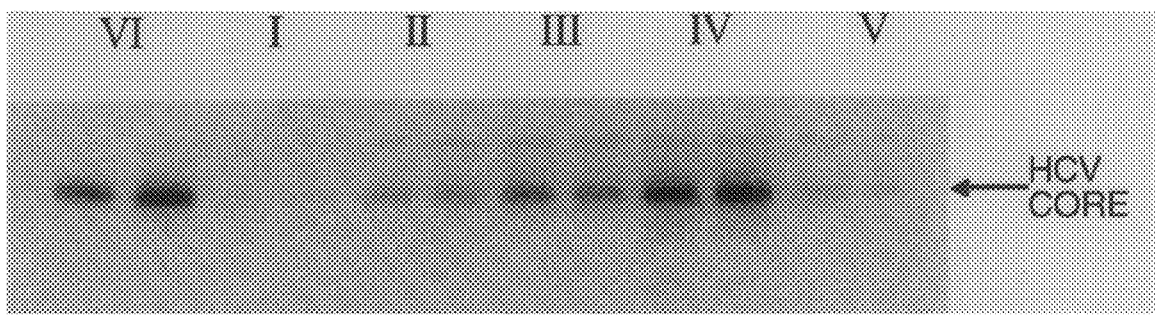
FIG. 10 is a photograph of an autoradiographic image of a SDS-polyacrylamide gel showing the inhibition of HCV core protein production by antisense HCV mRNA constructs. The Roman numerals refer to the different constructs displayed in FIG. 9. HCV core protein was translated from "wild type" 1b (II) IRNA, separated on SDS-PAGE, and quantitated by densitometric scanning.

These antisense mRNA-Producing constructs were transcribed, and the resulting transcripts tested for the ability to inhibit translation of "wild type" 1b (II) HCV mRNA in a rabbit reticulocyte lysate system, using the method described above. The results are presented in FIG. 10. Densitometric analysis of HCV core protein translated from "wild type" 1b (II) mRNA and separated on SDS-PAGE revealed an approximate 90 and 95% reduction in HCV core protein by the formation of mRNA hybrids by antisense constructs I (SEQ ID NO: 39) and V (SEQ ID NO: 43), respectively. These results suggest that antisense HCV mRNA has the potential of exhibiting very potent antiviral effects.

Figure 11:
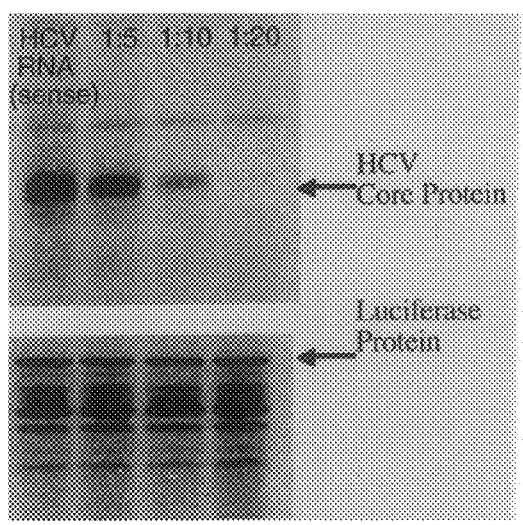
FIG. 11 is a photograph of an autoradiographic image of a SDS-polyacrylamide gel showing the inhibition of HCV wild type 1b mRNA translated in a rabbit reticulocyte lysate system. There was complete inhibition at a 1:20 ratio of target mRNA to antisense HCV construct I of 1:20 (top). There was no effect of construct I on translation of luciferase uRNA at the same ratio (bottom). The top arrow points to the HCV core protein band; the bottom arrow points to the luciferase protein band.

The specificity and properties of inhibition by antisense RNA (I) (SEQ ID NO: 39) was studied in greater detail. Inhibition of "wild type" 1b HCV mRNA translation was measured by the amount of HCV core protein produced in a rabbit reticulocyte lysate system and analyzed on SDS-PAGE (FIG. 11). There was a progressive decrease in "wild type" 1b HCV mRNA translation when the target to antisense RNA molar ratio was increased from 1:5 to 1:20. At a 1:20 molar ratio, inhibition of core protein translation was complete. In contrast, antisense RNA (I)(SEQ ID NO: 39) had no effect on luciferase mRNA translation at the same molar ratios (FIG. 11, bottom), demonstrating that the antisense mRNA antiviral effects were specific.

EXAMPLE III

Further Methods for Measuring the Effects of Antisense Oliconucleotides on HCV Expression Development of Reagents for in vitro and in vivo Studies:

The effect of antisense oligonucleotides on HCV RNA translation can be assessed by monitoring production of a structural viral protein, using, for example, either immunodetection or by an enzymatic assay based on an enzyme fused to the viral protein.

A. Immunodetection: Three novel monoclonal antibodies (MABs) were established against a recombinant hepatitis C virus (HCV) core protein derived from cloned type 1b HCV cDNA. MABs C7-50 and C8-59 recognize a conserved linear epitope represented by amino acid residues 21 to 40 of the core protein. MAB C8-48 is directed against a strain-specific conformational epitope located within the first 82 amino acids of the core protein. The 82 amino acid sequence is: MSTNPKPQRKTHRNTNRRPPDVKF-PGGGQIVGGVYLMPRRGPKLG VRAPRKTSER-SQPRGRRQPIPKARRPEGRTWAQPGYP (SEQ ID NO: 44).

Figure 12:
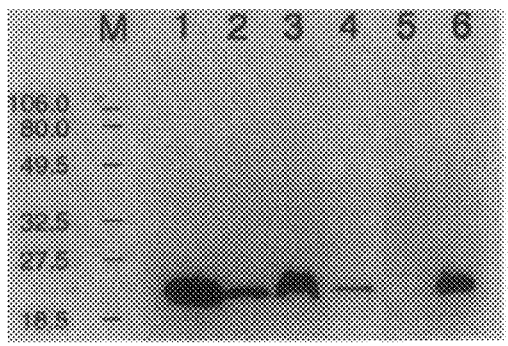
FIG. 12 is a photograph of an autoradiographic image of a SDS-polyacrylamide gel showing HCV gene expression in pBKCMVTH-transfected human HCC cell lines and in primary adult rat hepatocytes (PARH). The cell lines in each lane are: HuH-7 (lane 1); Hep G2 (land 2); FOCUS (lane 3); and PARH (lane 4).

HCV core gene expression was analyzed by Western immunoblotting or by indirect immunofluorescence microscopy in transfected human hepatocellular carcinoma cell lines (HCC) and primary adult rat hepatocytes (PARH) (FIG. 12). Each cell line was transiently transfected with the CMV promoter-driven expression construct pBKCMVTH, which was made as follows. The vector pBKCMV (Stratagene, La Jolla, Calif.) was used to prepare an eukaryotic HCV core expression construct. The lac promoter was removed by digestion of the vector with NheI and SalI, followed by filling in of the recessed 3' termini by the Klenow DNA polymerase reaction and self-ligation. A stop codon linker was then inserted into the ApaI-KpnI sites. This modified vector was named pBKCMVΔlacPSTP. An HCV cDNA containing nucleotide position 1 to 1321 (Wakita and Wands, supra) was subcloned into the BamHI-XbaI sites of pBKCMVΔlacPSTP to yield plasmid pBKCMVTH.

FIG. 12 is a Western blot of an SDS-PAGE gel, showing the amount of HCV core protein expressed from each of the following pBKCMVTH-transfected cell types: HuH-7 (lane 1), Hep G2 (lane 2), FOCUS cells (lane 3), and PARH (lane 4). Cell lysates were prepared 48 hours after transfection and analyzed by 15% SDS-PAGE and Western immunoblotting using MAB C7-50. HuH-7 cells mock-transfected with pBKCMVTHlac PSTP (lane 5) and in vitro translated HCV core protein (lane 6) served as negative and positive controls, respectively. Molecular weight standards in kDa are shown on the left.

Immunodetection can also be used to detect microscopically the amount of HCV core protein expressed in a cell. For example, indirect immunofluorescent staining was used to measure the amount of HCV core protein expressed in pBKCMVTH-transfected HuH-7 cells (FIG. 13). HuH-7 cells were grown on microscope cover slides and transiently transfected with pBKCMVTH. The cells were processed 48 hours after transfection before detecting HCV core protein with the fluorescent-tagged monoclonal antibody MAB C7-50, as described above. Fluorescent tagging can be performed according to standard methods known to those skilled in the art. In FIG. 13, photographs A and B show a typical granular cytoplasmic staining pattern. In Photograph C, non-transfected cells were counterstained with Evans Blue to serve as negative controls. A vesicular staining pattern is apparent in photographs B and C, and is especially prominent in photograph D. Vesicular structures of varying amounts and size were found together with a granular cytoplasmic staining pattern in all transfected cell lines examined. These vesicles gave a ring-like fluorescent pattern and contained an empty inner space, suggesting that core protein is associated with a vesicle membrane.

B. Enzymatic Assay: To facilitate and render more sensitive the quantitation of inhibition of HCV gene expression by antisense oligonucleotides, the construct pCMVTHluc+ was made. Construct pCMVTHluc+ includes the HCV 5' noncoding region, and the translated region which encodes the first 82 amino acids of the core protein (SEQ ID NO: 44) fused in frame to the firefly luciferase gene. The luciferase translation initiation codon had been deleted by recombinant polymerase chain reaction technology. Translation of HCV-luciferase fusion RNA in vitro or in the cell produces luciferase activity that can be measured by a standard enzymatic assay (Ausubel et al., eds. *Current Protocols in Molecular Biology*, John Wiley and Sons, Inc., N.Y.). Expression of this construct can be blocked by antisense oligonucleotides or RNA constructs in vitro. This construct can be cotransfected with antisense RNA-expressing constructs into cells in culture, and effects of these constructs on translation of the target RNA can be measured by a luciferase assay. As an internal control for varying transfection efficiencies, a plasmid encoding the lacZ gene under control of an SV40 promoter (pSVβgal; Promega, Madison, Wis.) is cotransfected in these experiments. The pSVpgal reporter construct codes for β-galactosidase, whose expression in the cell can be quantitatively assessed by standard enzymatic assays known to those skilled in the art (Promega Corp., *Promega Protocols and Applications Guide*, 2d ed. Madison, Wis.). Additional enzymatic assays can be designed according to the same principle, using alternative reporter enzymes known to those skilled in the art in place of the luciferase enzyme used above.

Use of Stable Cell Lines in Culture, and in an Animal Model, for Testing Antisense Oligonucleotides for the Ability to Inhibit HCV Translation:

Oligonucleotides of the invention can be tested in any cell line expressing HCV, examples of which are known to the art. For example, cells that express HCV under the control of an inducible promoter, e.g., the tetracycline promoter, are useful for screening the HCV-inhibitory effects of the oligonucleotides of the invention.

An HCV cDNA which contained the 5' noncoding region and coding regions for the core protein and a portion of the envelope protein (nt 1-1321; Wakita and Wands, supra) was cloned into the vector pUHD10-3 (Gossen et al., supra), which allows transcription of an inserted cDNA under control of a tightly regulated promoter in cell lines constitutively expressing a tetracycline-controlled transactivator (see Gossen et al., *Proc. Natl. Acad. Sci.* 89:5547–5551, 1992). This construct, named pUHDTH, was used to raise a stable cell line termed UTH-28. Expression of HCV cDNA can be monitored by immunoblotting of processed viral core protein using the monoclonal antibody C7-50. Core protein production can be measured by densitometry scanning of Western blots, thereby serving as an indicator of translation from the viral RNA target sequence in the cell. The amount of target RNA present in the cell can be regulated by the concentration of tetracycline in the culture medium.

ODNs can be used to inhibit HCV mRNA translation in cells stably transfected with a vector bearing HCV sequences, e.g., UTH-28 cells (FIG. 13). A phosphorothioate modified A367 ODN was compared to the native phosphodiester A367 with respect to its effect on translation of HCV sequences. Cells were derepressed by removal of tetracycline from the medium, and the A367 and S351 ODNs (17 nt each) were added to a concentration of 2 μM and transfected by calcium phosphate precipitation. HCV core protein levels were measured in cell lysates by Western blots after a six hour incubation with anti-HCV core MAB C7-50. In FIG. 14, lanes 1 and 2 show no effect of native phosphodiester ODNs A367 and S351 on HCV core expression. This result is most likely an experimental artifact, the unmodified phosphodiester ODNs being rapidly degraded by nucleases present in the serum used to supplement the culture medium. However, phosphorothioate-modified ODNs, being more resistant to degradation, do show an effect under these conditions. Lane 3 shows an 85% reduction of HCV core antigen expression exhibited by the phosphorothioate-modified A367 compared to the phosphorothioate-modified sense S351 ODN (lane 9). In lane 5 are untreated cells, and in lane 6 are cells treated with tetracycline. There is complete suppression of HCV core protein expression, demonstrating that the promoter is not "leaky". These results establish that if an HCV-specific antisense, but not sense, ODN reaches sufficient intracellular levels, there is a potent antiviral effect within the cell.

Other stable cell lines for testing HCV inhibitory reagents can be constructed, e.g., by transfecting other types of tumor cells with HCV cDNA containing the 5' noncoding region and coding sequences for at least a portion of the core protein, as described herein. Alternative tumor cells lines include, but are not limited to, liver cancer-derived cell lines such as HuH-7 or Hep G2.

Animal Models for Testing Antisense Oligonucleotides:

Stable cell lines expressing HCV under the control of an inducible promoter, e.g., the UTH-28 cells discussed above, can be injected into animals, e.g., mice, particularly nude mice, for screening the effect of antisense oligonucleotides on HCV expression in vivo. UTH-28 cells grow in the liver of the mouse. HCV expression in these cells is induced by tetracycline removal, i.e., by removing tetracycline from the animal's drinking water. Alternative animal models can be constructed by transfecting the HCV-expressing constructs described herein into other tumor cell lines, and injecting the transfected cell line into the appropriate animal species.

Antisense oligonucleotides of the invention can also be tested in animals that are naturally infected with HCV, e.g., in chimpanzees, by administering the oligonucleotides to the animal by one of the methods discussed above, and by any other methods known to those skilled in the art.

Other Embodiments

From the above description, one skilled in the art can easily ascertain the essential characteristics of the present invention, and without departing from the spirit and scope thereof, can make various changes and modifications of the invention to adapt it to various usages and conditions.

It is understood that oligonucleotides having minor variations from the disclosed sequences which do not affect the biological function (i.e., the ability of the oligonucleotide to hybridize to, and to inhibit the translation of, HCV RNA) of the oligonucleotides are within the invention.

All publications cited herein are fully incorporated by reference herein in their entirety. Other embodiments are in the claims set forth below.

TABLE I

Percent Inhibition of Type II and III HCV Translation by oligonucleotides

| | | | Inhibition of protein synthesis [b] (%) | |
|---|---|---|---|---|
| Oligos[a] | Size (nt) | GC (%) | Type II | Type III |
| SEQ ID NO: 1 | A37 | 28 | 57 | 5 | ND |
| SEQ ID NO: 2 | A65 | 28 | 54 | 7 | 54 |
| SEQ ID NO: 3 | A81 | 28 | 46 | 40 | 16 (1)[c] |
| SEQ ID NO: 4 | A103 | 28 | 50 | −1 | −1 (1) |
| SEQ ID NO: 5 | A147 | 28 | 71 | 20 | 14 |
| SEQ ID NO: 6 | A161 | 28 | 61 | 81 | 76 |
| SEQ ID NO: 7 | A175 | 28 | 57 | 55 | 88 |
| SEQ ID NO: 8 | A211 | 28 | 61 | 4 | −20 |
| SEQ ID NO: 9 | A242 | 28 | 68 | 34 | ND |
| SEQ ID NO: 10 | A270 | 28 | 57 | 44 | ND |
| SEQ ID NO: 11 | A298 | 28 | 54 | 40 | 35 |
| SEQ ID NO: 12 | A312 | 28 | 57 | 45 | 18 |
| SEQ ID NO: 13 | A326 | 28 | 71 | 64 | 30 |
| SEQ ID NO: 14 | A339 | 27 | 70 | 53 | 50 |
| SEQ ID NO: 15 | A349 | 28 | 61 | 41 | 39 (1) |
| SEQ ID NO: 16 | A367 | 27 | 44 | 98 | 95 (1) |
| SEQ ID NO: 17 | A377 | 27 | 30 | 80 | 94 |
| SEQ ID NO: 18 | A387 | 27 | 37 | 15 | 22 (2) |
| SEQ ID NO: 19 | A446 | 27 | 52 | 13 | 4 (3) |
| SEQ ID NO: 29 | S38 | 28 | 54 | −4 | ND |
| SEQ ID NO: 30 | S54 | 28 | 46 | 0 | ND |
| SEQ ID NO: 31 | S76 | 28 | 50 | 2 | −15 |
| SEQ ID NO: 32 | S120 | 28 | 71 | −21 | −2 |
| SEQ ID NO: 33 | S148 | 28 | 57 | −11 | 29 |
| SEQ ID NO: 34 | S271 | 28 | 54 | −30 | −33 |
| SEQ ID NO: 35 | S291 | 28 | 68 | −37 | −33 |
| SEQ ID NO: 36 | S312 | 28 | 68 | −35 | −25 |

[a] A = Antisense oligo, S = sense oligo. The number after A or S indicates the position of the 5' end of the oligo.
The underlining indicates oligos that inhibit HCV type II and III translation by greater than 50%.
[b] Inhibition assays were performed as described in materials and methods. Each oligo was used at 10 fold molar excess relative to HCV RNA. ND = not determined.
[c] The numbers in parentheses indicate the mutations in the target sequence of the type III clone.

TABLE II

Inhibition of HCV and Luciferase RNA translation by antisense oligos, and effect of the annealing step on the inhibition of HCV RNA translation

| | | Inhibition of translation (%) | | |
|---|---|---|---|---|
| | | annealing(+) | annealing(−) | Luciferase[a] |
| SEQ ID NO: 2 | A65 | 75 | 73 | −2 |
| SEQ ID NO: 6 | A161 | 77 | 83 | −27 |
| SEQ ID NO: 14 | A339 | 60 | 63 | −84 |
| SEQ ID NO: 17 | A377 | 84 | 93 | −49 |

[a] All in vitro translations with luciferase RNA were performed with annealing steps

What is claimed is:

1. An oligonucleotide that hybridizes to Hepatitis C Virus RNA under physiological conditions, said oligonucleotide being an RNA or a DNA molecule comprising a sequence selected from the group consisting of SEQ ID NOs: 1–4 and 6–20, said oligonucleotide being no more than 28 nucleotides long.

2. The oligonucleotide of claim 1, wherein the nucleotide sequence of said oligonucleotide comprises a nucleotide sequence selected from the group consisting of SEQ ID NOs: 2, 6, 7, 14, 16, 17, and 20.

3. The oligonucleotide of claim 1, wherein the nucleotide sequence of said oligonucleotide consists of SEQ ID NO: 2.

4. The oligonucleotide of claim 1, wherein the nucleotide sequence of said oligonucleotide consists of SEQ ID NO: 6.

5. The oligonucleotide of claim 1, wherein the nucleotide sequence of said oligonucleotide consists of SEQ ID NO: 7.

6. The oligonucleotide of claim 1, wherein the nucleotide sequence of said oligonucleotide consists of SEQ ID NO: 14.

7. The oligonucleotide of claim 1, wherein the nucleotide sequence of said oligonucleotide consists of SEQ ID NO: 16.

8. The oligonucleotide of claim 1, wherein the nucleotide sequence of said oligonucleotide consists of SEQ ID NO: 17.

9. The oligonucleotide of claim 1, wherein the nucleotide sequence of said oligonucleotide consists of SEQ ID NO: 20.

10. The oligonucleotide of claim 1, wherein the nucleotide sequence of said oligonucleotide comprises a nucleotide sequence selected from the group consisting of SEQ ID NOs: 1, 3, 8–13, 15, 18, and 19.

11. A vector comprising a nucleotide sequence which is transcribed in an animal cell to generate the oligonucleotide of claim 1, said oligonucleotide being an oligoribonucleotide.

12. The vector of claim 11, wherein said vector is an adenovirus vector.

13. The vector of claim 11, wherein said transcribed nucleotide sequence is operably linked to a transcription control sequence that functions in hepatocytes.

14. The vector of claim 13, wherein said transcriptional control sequence comprises a cytomegalovirus promoter.

15. The oligonucleotide of claim 1, wherein said oligonucleotide is an oligodeoxynucleotide.

16. The oligonucleotide of claim 1, wherein said oligonucleotide is an oligoribonucleotide.

17. The oligonucleotide of claim 1, wherein said oligonucleotide is a phosphorothioate oligonucleotide.

18. The oligonucleotide of claim 1, wherein said oligonucleotide is a methylphosphonate oligonucleotide.

19. An oligonucleotide consisting of SEQ ID NO: 23.

20. An oligonucleotide consisting of SEQ ID NO: 24.

21. An oligonucleotide consisting of SEQ ID NO: 26.

22. An oligonucleotide consisting of SEQ ID NO: 43.

23. An oligonucleotide that hybridizes to Hepatitis C Virus RNA under physiological conditions, said oligonucleotide being an RNA or a DNA molecule comprising a sequence selected from the group consisting of SEQ ID NOs: 39–42, said oligonucleotide being no more than 342 nucleotides long.

24. An oligonucleotide consisting of SEQ ID NO: 21.

25. An oligonucleotide consisting of SEQ ID NO: 22.

26. An oligonucleotide consisting of SEQ ID NO: 27.

27. An oligonucleotide consisting of SEQ ID NO: 28.

28. An oligonucleotide consisting of SEQ ID NO: 39.

29. An oligonucleotide consisting of SEQ ID NO: 40.

30. An oligonucleotide consisting of SEQ ID NO: 41.

31. An oligonucleotide consisting of SEQ ID NO: 42.

* * * * *